US008871501B2

(12) United States Patent
Claypool

(10) Patent No.: US 8,871,501 B2
(45) Date of Patent: Oct. 28, 2014

(54) PANELIZED DRUM SYSTEM

(76) Inventor: Rick Claypool, Sulphur Springs, TX (US)

(*) Notice: Subject to any disclaimer, the term of this patent is extended or adjusted under 35 U.S.C. 154(b) by 1113 days.

(21) Appl. No.: 12/113,941

(22) Filed: May 1, 2008

(65) Prior Publication Data

US 2011/0236965 A1    Sep. 29, 2011

Related U.S. Application Data

(60) Provisional application No. 61/025,700, filed on Feb. 1, 2008.

(51) Int. Cl.
| | | |
|---|---|---|
| C12M 3/00 | (2006.01) |
| C12M 1/00 | (2006.01) |
| C05F 17/02 | (2006.01) |
| C12M 1/12 | (2006.01) |
| C12M 1/107 | (2006.01) |
| C12M 3/04 | (2006.01) |

(52) U.S. Cl.
CPC ............ *C05F 17/0223* (2013.01); *C12M 23/06* (2013.01); *C12M 21/04* (2013.01); *C12M 23/34* (2013.01); *C12M 23/44* (2013.01); *C12M 27/10* (2013.01)
USPC .................. 435/290.3; 435/290.1; 435/291.8; 435/291.7; 435/298.2

(58) Field of Classification Search
CPC ... C05F 17/0223; C12M 21/04; C12M 23/06; C12M 23/34; C12M 23/44; C12M 27/10
USPC .......... 435/290.3, 294.1, 290.1, 291.8, 298.2, 435/291.7
See application file for complete search history.

(56) References Cited

U.S. PATENT DOCUMENTS

| | | | |
|---|---|---|---|
| 2,948,593 A | | 4/1957 | Larson |
| 3,245,759 A | | 4/1966 | Eweson |
| 3,890,129 A | * | 6/1975 | Chester ............................... 71/9 |
| 3,930,799 A | | 1/1976 | Eweson |
| 4,184,602 A | * | 1/1980 | Moliard ........................ 220/4.26 |
| 4,946,108 A | | 8/1990 | Koenig et al. |
| 5,022,982 A | | 6/1991 | Greeley |
| 5,047,349 A | | 9/1991 | Eweson |
| 5,169,782 A | | 12/1992 | Murphy et al. |
| 5,254,472 A | | 10/1993 | Brooks, III et al. |
| 5,346,305 A | * | 9/1994 | Chester ......................... 366/233 |
| 5,407,809 A | | 4/1995 | Finn |
| 5,589,391 A | * | 12/1996 | Fink ........................... 435/290.3 |
| 5,605,834 A | * | 2/1997 | Eberthson et al. .......... 435/290.3 |
| 5,762,225 A | * | 6/1998 | Byrd ................................. 220/6 |
| 6,110,733 A | | 8/2000 | Seymour |
| 7,371,566 B1 | * | 5/2008 | Craven, Jr. .................. 435/290.3 |
| 7,520,457 B1 | | 4/2009 | Poitras et al. |

(Continued)

FOREIGN PATENT DOCUMENTS

WO    WO-2005/113469 A1 * 12/2005

*Primary Examiner* — Nathan Bowers
(74) *Attorney, Agent, or Firm* — Salter & Michaelson

(57) ABSTRACT

A rotating drum that is made from a plurality of panels that are connected to form sub-cylinders that, in turn, are connected to form a drum cylinder. Drum heads are connected at both ends of the drum cylinders. The drum may be rotated using rotational means. In one preferred embodiment the rotational means is a tangential rotational drive system that engages drive tires that are positioned between sub-cylinders. A method for fabricating rotating drums. A business method of mass production of and/or distribution of rotating drums.

23 Claims, 18 Drawing Sheets

(56) References Cited

U.S. PATENT DOCUMENTS

2004/0029262 A1* 2/2004 Walker .................. 435/290.1
2007/0190643 A1* 8/2007 Noll ...................... 435/290.3
2008/0032375 A1* 2/2008 Hartmann et al. ......... 435/170

* cited by examiner

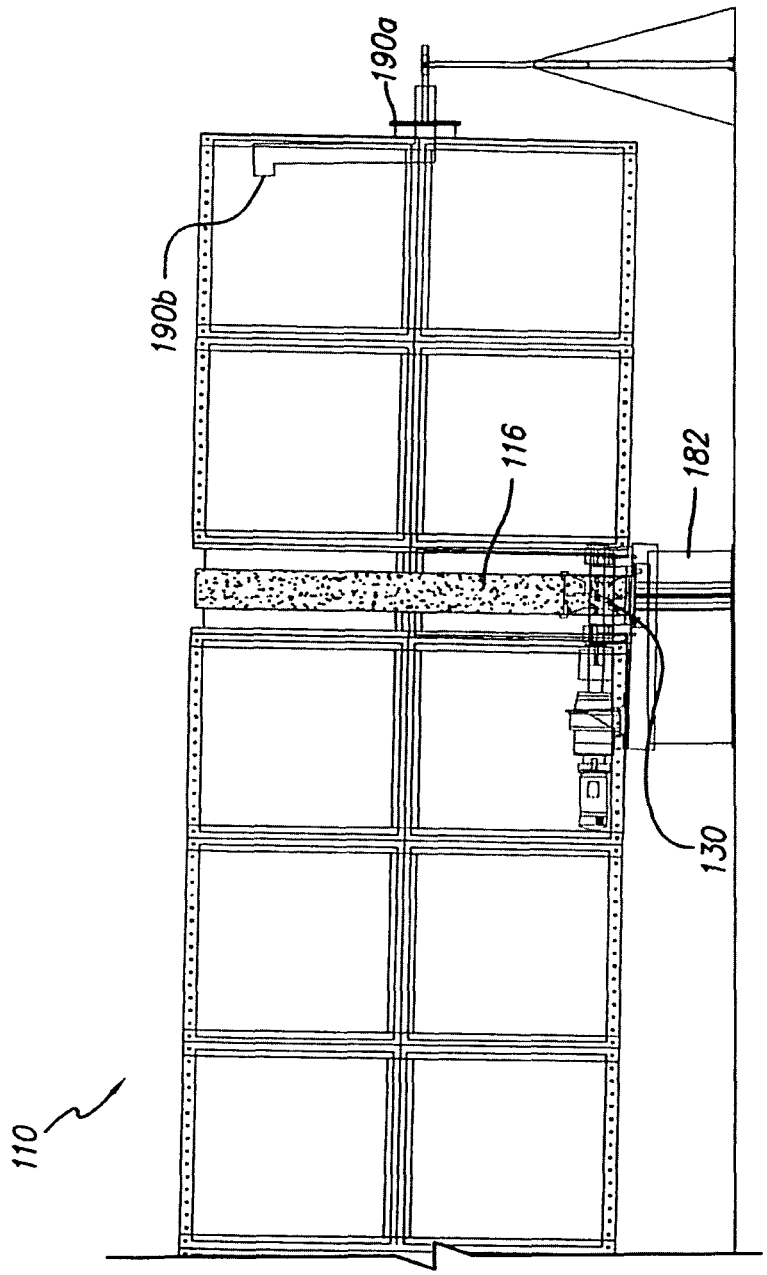

PANELIZED DRUM SYSTEM

The present application is an application claiming the benefit under 35 USC Section 119(e) of U.S. Provisional Patent Application Ser. No. 61/025,700, filed Feb. 1, 2008. The present application is based on and claims priority from this application, the disclosure of which is hereby expressly incorporated herein by reference in its entirety.

BACKGROUND OF INVENTION

The present invention is directed to a panelized drum system and, more particularly, to rotating drums as well as methods and apparatuses for fabrication of rotating drums using a panelized design and the principles of mass production and distribution.

Rotating drum composters (also known as "in-vessel composters") were first patented in 1870. Since then there have been over 177 patents issued in the United States for some part of the composting process. Exemplary composters are discussed in the following patents:

| U.S. Patent No. | Issue Date | Applicant(s) |
| --- | --- | --- |
| 2,948,593 | Apr. 15, 1957 | Larson |
| 3,245,759 | Apr. 12, 1966 | Eweson |
| 3,930,799 | Jan. 6, 1976 | Eweson |
| 5,047,349 | Sep. 10, 1991 | Eweson |
| 5,169,782 | Dec. 8, 1992 | Murphy et al. |
| 5,407,809 | Apr. 18, 1995 | Finn |
| 6,110,733 | Aug. 29, 2000 | Seymour |

The disclosures of the patents listed above are hereby expressly incorporated herein by reference in their entirety. These known composters can be divided into three categories: small composters, medium composters, and large composters. All the known composters have been fabricated one composter at a time. The known fabrication process for making a steel drum for small composters and medium composters comprises the following steps:
- cutting steel plates the length of the desired circumference of the sub-cylinder(s) that will form the body of the drum;
- rolling steel plates (putting a curve into flat plate—usually there is a section on both ends of the plate that is not rolled because of the limitation of the rolling machine),
- welding the ends of the steel plates together to form the sub-cylinder, and
- re-rolling the sub-cylinder to make it substantially round.

These steps are repeated until there are enough sub-cylinders to make the body of the drum (the "drum cylinder"). (It should be noted that because metal tends to stretch, in practice these sub-cylinders are rarely the same size. Also the process of re-rolling can be imprecise.) These sub-cylinders are then stacked end-to-end and welded together to form the body of the drum. (It should be noted that the welding process can correct some of the size and shape discrepancies between the sub-cylinders.) Typically, there are temporary fixtures that are placed inside the drum cylinder to achieve roundness. The drum cylinder is then capped on each end to create a drum. Doors and other accessories are then added to the drum and the complete drum is then sub-arc welded. Then the drum is sent to be painted and insulated. Significantly, known drums are fabricated one unit at a time and are virtually complete before they are painted and insulated. The typical rotating drum is rotated using systems such as a direct rotational drive system (such as a sprocket and chain drive), a large bull gear around the drum and a pinion gear, or those shown and described in the above incorporated references.

The small rotating drum composters are generally of a size that is easily transported from one place to the other. Small rotating drum composters are not very cost efficient.

The next size would be the medium rotating drum composters. Medium rotating drum composters are units that are still made the same way but these are not easily transported. They require special permits and equipment to transport them to the end user. Shipping medium rotating drum composters costs from $6,000 to $30,000.

The final size units are large rotating drum composters. These units are still manufactured in the same way but, because of their size, they cannot be transported after they have been fully assembled. Accordingly, large rotating drum composters are fabricated and welded together in the field (e.g. generally in a large area near a source of composting raw material). (For purposes of this disclosure, "in the shop" is defined as any process that takes place at the facility in which the product is made and "in the field" is defined as any place other than in the manufacturing facility (the shop) where the drum is to be located and used.) Even the painting and insulation has to be done in place, because once these large rotating drum composters are complete, they cannot be moved. This is an expensive and time-consuming process and is very weather dependant.

BRIEF SUMMARY OF THE INVENTION

A first preferred embodiment of the present invention is primarily directed to medium and large rotating drums, although the present invention may also include small rotating drums. The rotating drums may be used in applications such as composting. A second preferred embodiment of the present invention is primarily directed to the fabrication (which includes any type of manufacturing, making, building, constructing, or other means of creating) of rotating drums. A third preferred embodiment of the present invention is primarily directed to the business method of mass production of and/or distribution of rotating drums. These embodiments and other embodiments discussed herein are jointly referred to as the "panelized system" of the present invention.

One preferred embodiment of the present invention is a rotating drum that is made from a plurality of panels that are connected to form sub-cylinders. The sub-cylinders are, in turn, connected to form the drum cylinder. Drum heads are connected at both ends of the drum cylinders. The drum is then rotated using rotational means. In one preferred embodiment the rotational means is a tangential rotational drive system that engages drive tires that are positioned between sub-cylinders.

The foregoing and other objectives, features, and advantages of the invention will be more readily understood upon consideration of the following detailed description of the invention, taken in conjunction with the accompanying drawings.

BRIEF DESCRIPTION OF THE SEVERAL VIEWS OF THE DRAWINGS

FIGS. 15A-15B together are a side view of an exemplary rotating drum composter of the present invention.

DETAILED DESCRIPTION OF THE INVENTION

A first preferred embodiment of the present invention is primarily directed to medium and large rotating drums, although the present invention may also be directed to small rotating drums. The rotating drums may be used in applications such as composting. A second preferred embodiment of the present invention is primarily directed to the fabrication (which includes any type of manufacturing, making, building, constructing, assembling, or other means of creating) of drums. The fabrication may include two separately unique stages: fabrication of the components of the drums and fabrication of the drum itself. A third preferred embodiment of the present invention is primarily directed to the business method of mass production of and/or distribution of the drums. These embodiments and other embodiments discussed herein are jointly referred to as the "panelized system" of the present invention.

Figure 2:
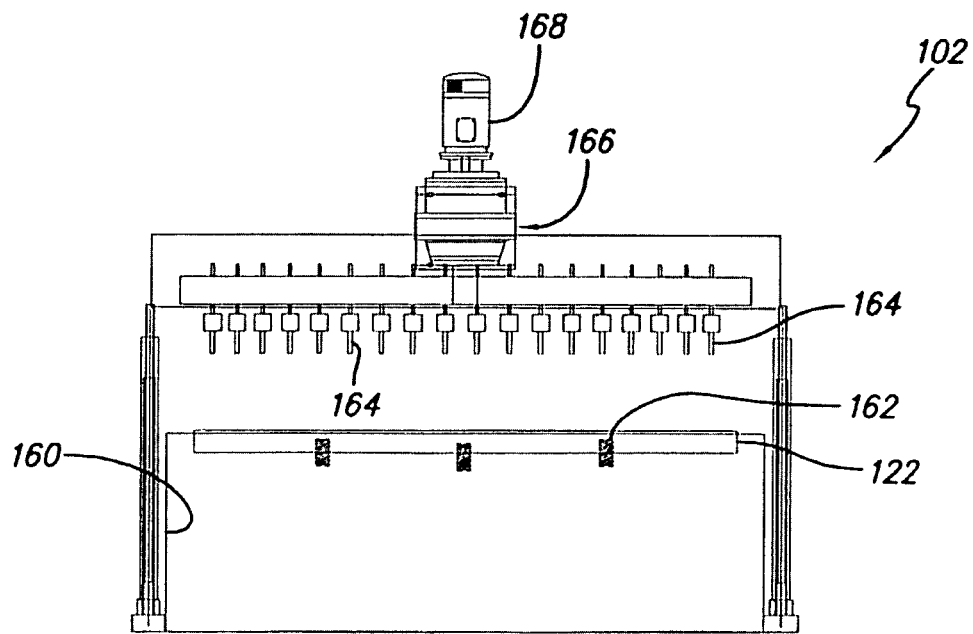
FIG. 2 is a side view of an exemplary multi-head drill press.
Figure 3:
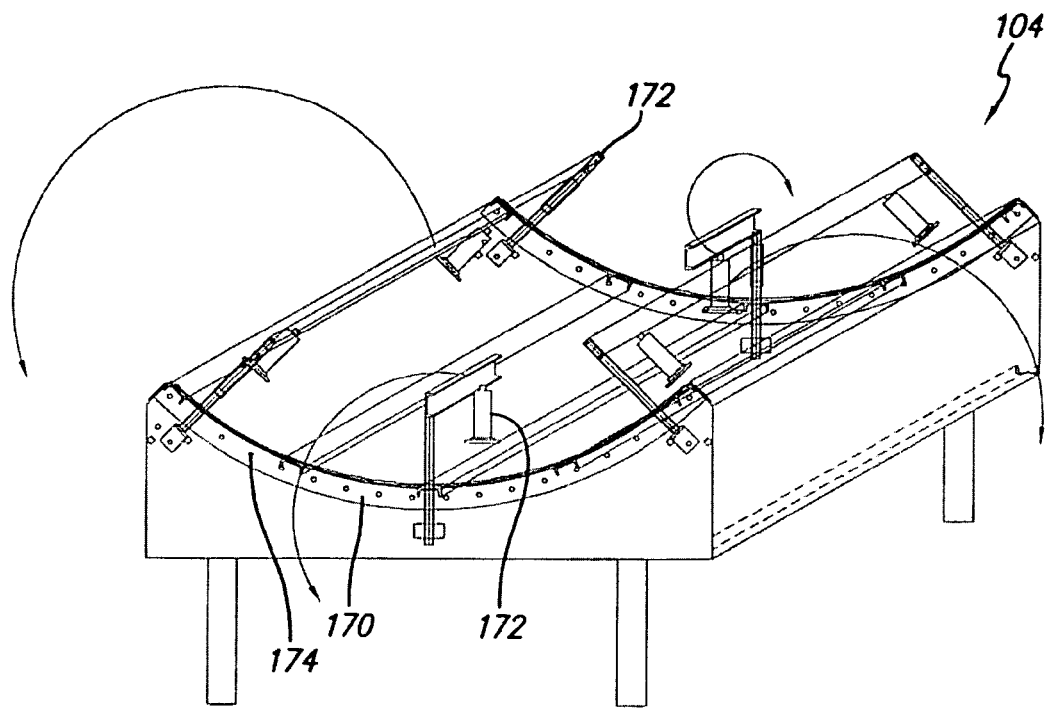
FIG. 3 is a perspective view of an exemplary welding table.
Figure 4:
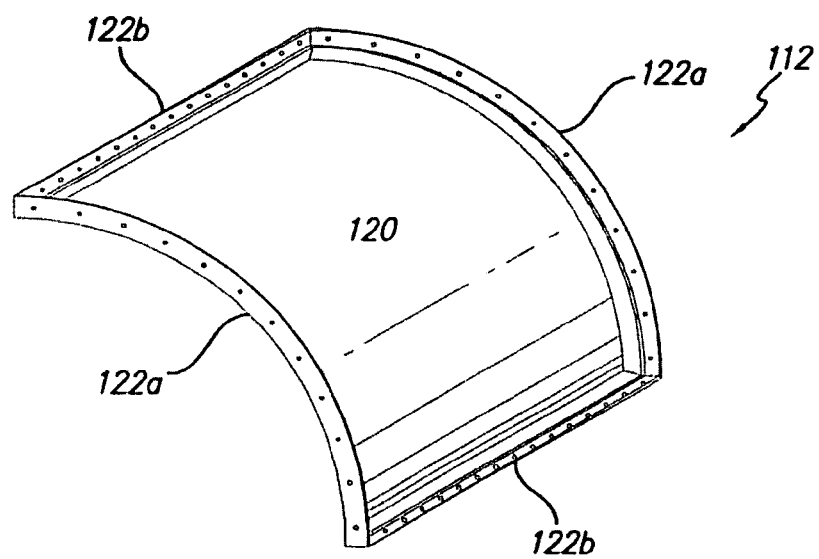
FIG. 4 is a perspective view of an exemplary single panel.
Figure 5A:
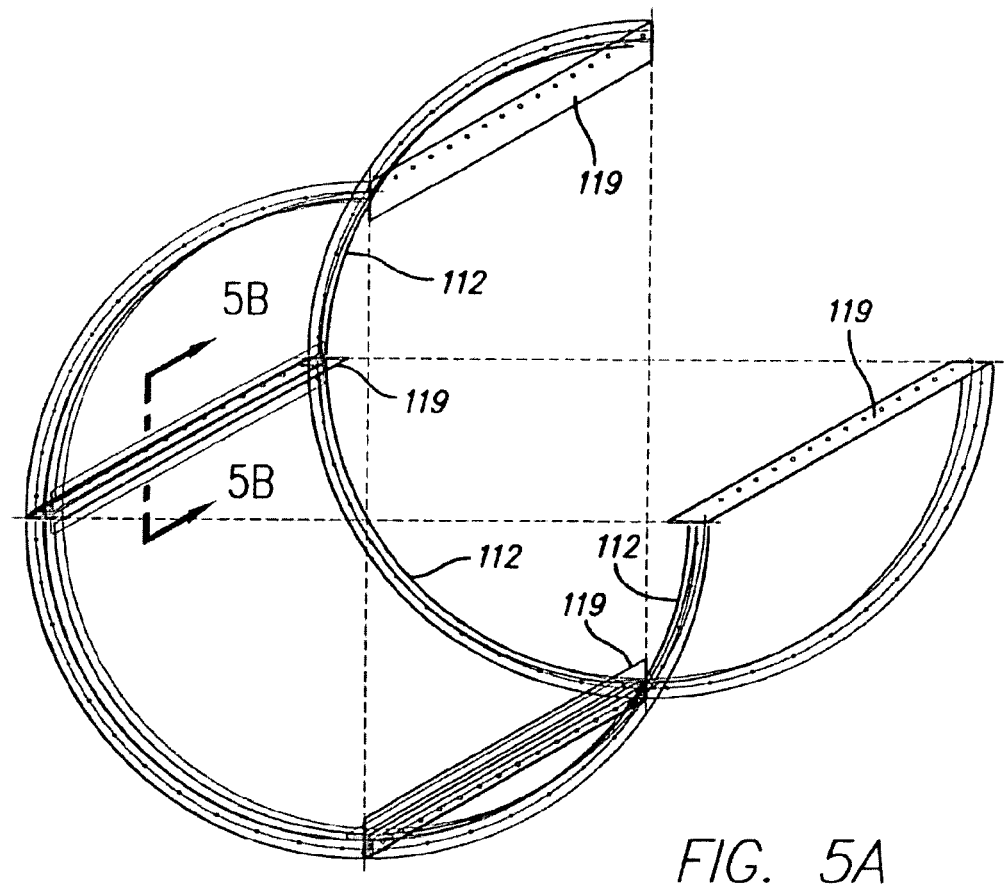
FIG. 5A is a perspective view of three panels such as those shown in FIG. 4, the three panels assembled together to make three-quarters of a ring or sub-cylinder.

Central to the panelized system of the present invention is the use of fixtures such as the novel cutting table 100 (FIG. 1), the novel multi-head drill press 102 (FIG. 2), the novel welding table 104 (FIG. 3), and other fixtures that may be used for mass production of components of a drum 110. Also central to the panelized system is the fact that the drums 110 are constructed from a plurality of "panels" (referred to generally as panels 112) such as those shown in FIG. 4. In addition to the panels 112, the drum 110 includes components such as drum heads 114 (also referred to as an "end cap") and drive tires 116 (also referred to as "load bearing rings"). Summarily, at least the panels 112 are preferably fabricated using the principles of mass production. Each panel 112 is fabricated so as to ensure that it is interchangeable with any other panel 112. (FIG. 5A shows three panels secured together, but any of the panels shown in FIG. 6 would fit as the fourth panel to form a sub-cylinder 118.) The panel 112 (and other components such as a drum head 114) may then be painted and insulated. Then, the panel 112 is stacked together with other panels 112 so that the stacked panels 112 (FIG. 6) can easily fit into any shipping container and shipped anywhere in the world at standard shipping rates. The drum heads 114 and drive tires 116 are also preferably fabricated so that the components are inter-changeable and can fit into a shipping container. All components of a rotating drum 110 are shipped to the end user. The end user then removes the components from the container and assembles (e.g. using connectors 117 such as bolts or other connection mechanisms) the components together "in the field." Once the connectors are in place, the rotating drum composter is ready to operate. While it is possible for the end user to actually assemble the rotating drum composter, normally the rotating drum composter is installed with manufacturer-trained supervision.

Although composters have been around since 1870, it is only in the last few years that the demand for composters has skyrocketed. Until now, a composter manufacturer having about forty employees could make approximately one composter a month. This amount of production met the demand of the times. But as the value of composting is being realized by different industries, that same composter manufacturer is being asked to produce a hundred composters in a single year. The composter manufacturer just cannot meet this demand using the old system.

Using the panelized system of the present invention, twenty employees could fabricate one composter a week. Using old technology fixtures or tools to build such a large scale panelized system would have been daunting because of the precision required. But using the fixtures or tools (the cutting table 100 (FIG. 1), the multi-head drill press 102 (FIG. 2), and the welding table 104 (FIG. 3)) described herein, the precision necessary to implement the panelized system of the present invention can be realized.

Further, it should be noted that the panelized system of the present invention is more than just dividing known rotating drum systems into a plurality of panels 112. For example, known rotating drum systems are not painted and insulated until after they have been assembled. The reason for this is that the welding process causes the paint and the insulation to burn (as they are flammable). The panelized system of the present invention does not typically require welding to join the panels 112 together.

Drum Components

Figures 7A, 7B:
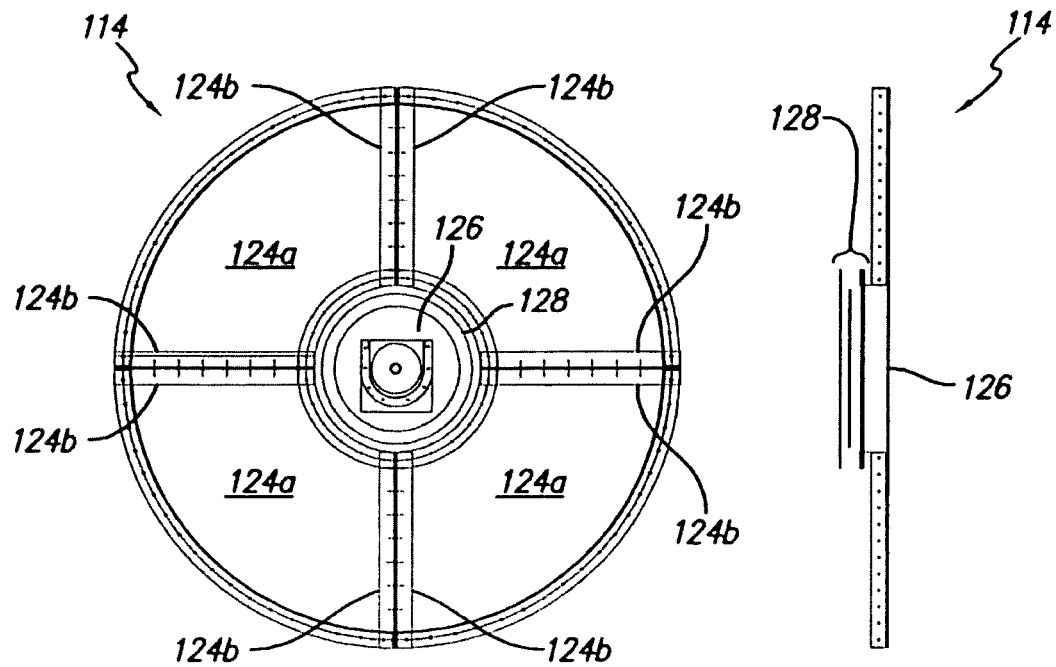
FIG. 7A is a front view of an exemplary drum head (or end cap).
FIG. 7B is a side view of the exemplary drum head of FIG. 7A.
Figure 8:
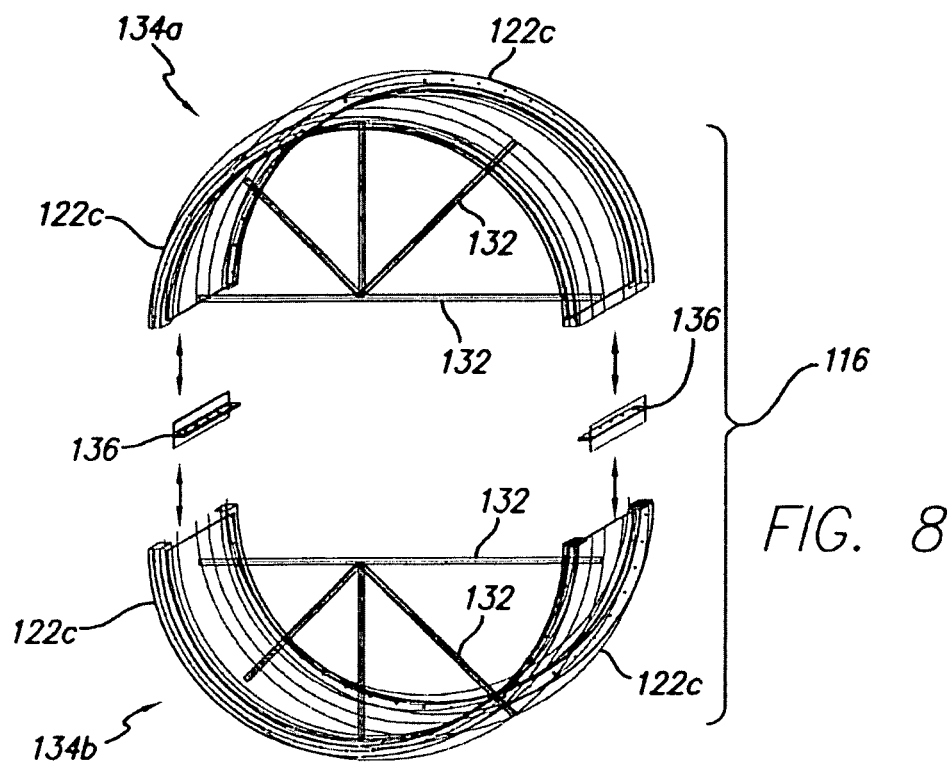
FIG. 8 is a perspective view of an exemplary drive tire or load bearing ring in expanded form.

The primary components of a drum 110 are the panels 112 (FIGS. 4-6), the drum heads 114 (FIG. 7A and FIG. 7B), and the drive tires 116 (FIG. 8). There are also connectors 117 (e.g. bolts) and baffle bars 119.

The panels 112 of the present invention are preferably fabricated out of rolled plate 120 (which is actually rolled flat plate 120 in the shown embodiments) and angle iron 122 (shown as two elongated legs arranged at a right angle on their respective longitudinal edges). The angle iron 122 can be thought of as a frame and the rolled plate 120 can be thought of as a skin that spans the opening created by the frame (a spanning skin). The rolled plate 120 forms the expanse of the panel 112 and the angle iron 122 forms the edging flange of the panel 112. It should be noted that alternative materials may be used as such as long as the material has sufficient strength, durability, and structural integrity. The angle iron 122 substantially borders all edges of the rolled plate 120. In one preferred embodiment, there are rolled pieces of angle iron 122a (along the edge that will be the circumferential edges of the sub-cylinders 118 or frame sides) and straight pieces of the angle iron 122b (along the edge that will be between the panels 112 of the sub-cylinders 118 or frame ends).

To optimize the panelized system of the present invention, all the panels 112 should be substantially the same size in order for them to mate together properly in the field. While there are a number of ways to make the panels 112 and different types of panels may be used (see the "variations" section below), the principle is that the panels should be substantially uniform (e.g. to within tolerances).

One of the advantages of using angle iron 122 and rolled plate 120 to form the panel 112 is that it allows for greater tolerances: if the rolled plate 120 is not exactly square, the legs of the angle iron 122 provide "leeway" to help correct the imprecision. In other words, if one side of the rolled plate 120 is 0.5 inches (1.27 centimeters) shorter than the other sides, the longitudinal corner between the legs of the angle iron 122 would be slightly off the edge of the rolled plate 120 with the leg of the angle iron 122 extending beyond the edge of the rolled plate 120 to compensate for the missing portion of the edge of the rolled plate 120.

FIG. 5A is a perspective view of three panels 112 assembled together to make three-quarters of a ring or sub-cylinder 118. Four panels 112 would be used to form the complete sub-cylinder 118. Although the shown embodiment uses four panels 112, a sub-cylinder 118 may be designed to use any number of panels. For example, a sub-cylinder 118 with a large diameter may be constructed from five or six panels. This would reduce the size of the panels and thus be advantageous for panel fabrication and drum distribution. On the other hand, a sub-cylinder 118 with a small diameter may be constructed from three panels. This would be advantageous in drum fabrication (e.g. less components to assemble).

Figure 5B:
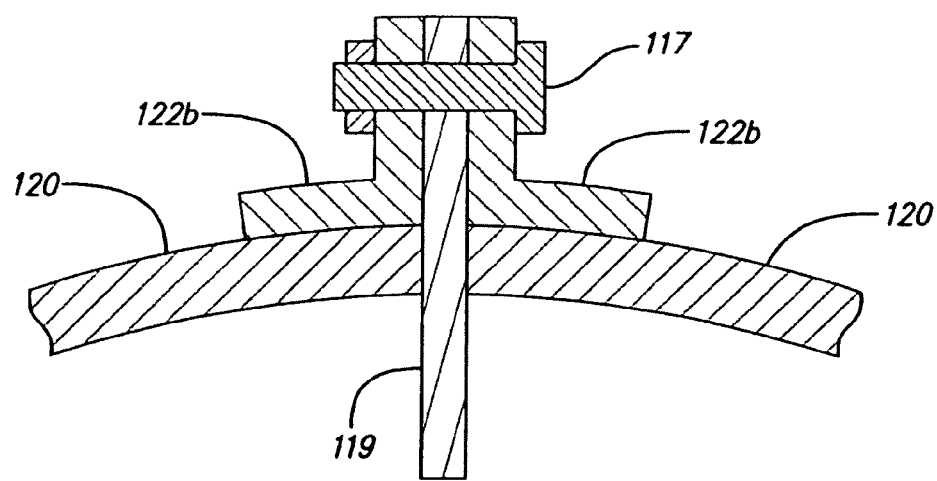
FIG. 5B is a cross-sectional view of two panels joined with a baffle bar therebetween taken along line 5B-5B of FIG. 5A.

FIG. 5B is a cross-sectional view of two panels 112 (the respective rolled plate 120 and angle iron 122b being shown) joined with a baffle bar 119 therebetween by a connector 117. The purpose of the baffle bars 119 is to cause the material inside the drum composter to tumble as it progresses through the composter. Tumbling creates better aeration than the sliding that would occur without the baffle bars 119. In one preferred embodiment, the baffle bar 119 is substantially coextensive with straight pieces of the angle iron 122b. As shown in FIG. 5A, a separate baffle bar 119 may be positioned between each set of panels 112. It should be noted that, instead of multiple baffle bars 119, elongated baffle bars 119" (FIG. 14) could extend between multiple sub-cylinders 118. It should be noted that, although the rolled plate 120 is shown to be touching the baffle bar 119 in FIG. 5B, the rolled plate 120 would not necessarily have to be touching and/or adjacent the baffle bar 119 because the angle iron 122b allows for leeway in imperfections and irregularities in the "squareness" of the rolled plate 120.

Figure 9:
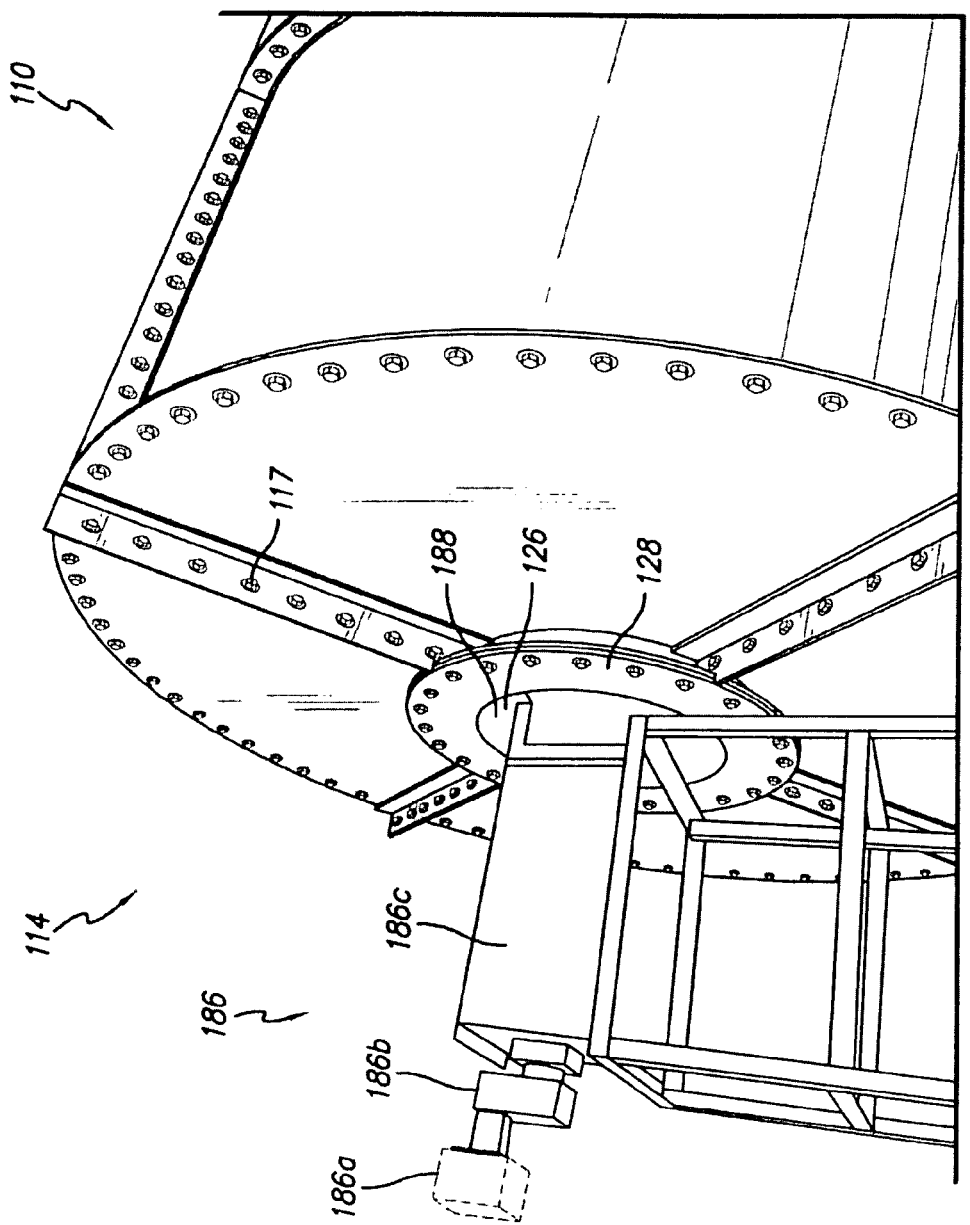
FIG. 9 is a perspective view of an exemplary drum head of the present invention along with a motor, gearbox, and screw conveyor.

Preferred embodiments of the drum heads 114 (e.g. as shown in FIG. 7A, FIG. 7B, and FIG. 9) are made by cutting a wedge 124a out of flat plate and drilling holes therein. (It should be noted that in the preferred embodiment the "wedge" is not a true wedge as it has a wedge-shaped portion of the tip removed to create a substantially circular opening 126 when multiple wedges 124a are joined.) The drilling of the holes in the wedges 124a may be accomplished on the same fixture and/or a fixture similar to the multi-head drill press 102 shown in FIG. 2. The holes are shown as having been drilled along the rounded edges of the wedges 124a. The drum heads 114 have angle iron 124b substantially adjacent the straight edges of the wedges 124. As with the panels 112, the use of the angle iron 124b allows for leeway if the wedges 124a are not precisely cut. The cutting of the angle iron 124b may be accomplished on the same fixture or a fixture similar to the cutting table 100 shown in FIG. 1. The drilling of the angle iron 124b may be accomplished on the same fixture and/or a fixture similar to the multi-head drill press 102 shown in FIG. 2. As with the panels 112, the drum heads 114 are fabricated so that the pieces are interchangeable and can fit into a shipping container. In the shown embodiment, four wedges 124a and eight pieces of angle iron 124b are used. A drum head 114 may be assembled from the wedges 124a and angle iron 124b on the same fixture or a fixture similar to the welding table 104 shown in FIG. 3. The angle irons 124b are connected together as shown using connectors 117, but without baffle bars 119. The circular opening 126 is preferably ringed by sealing structure 128.

Figure 10:
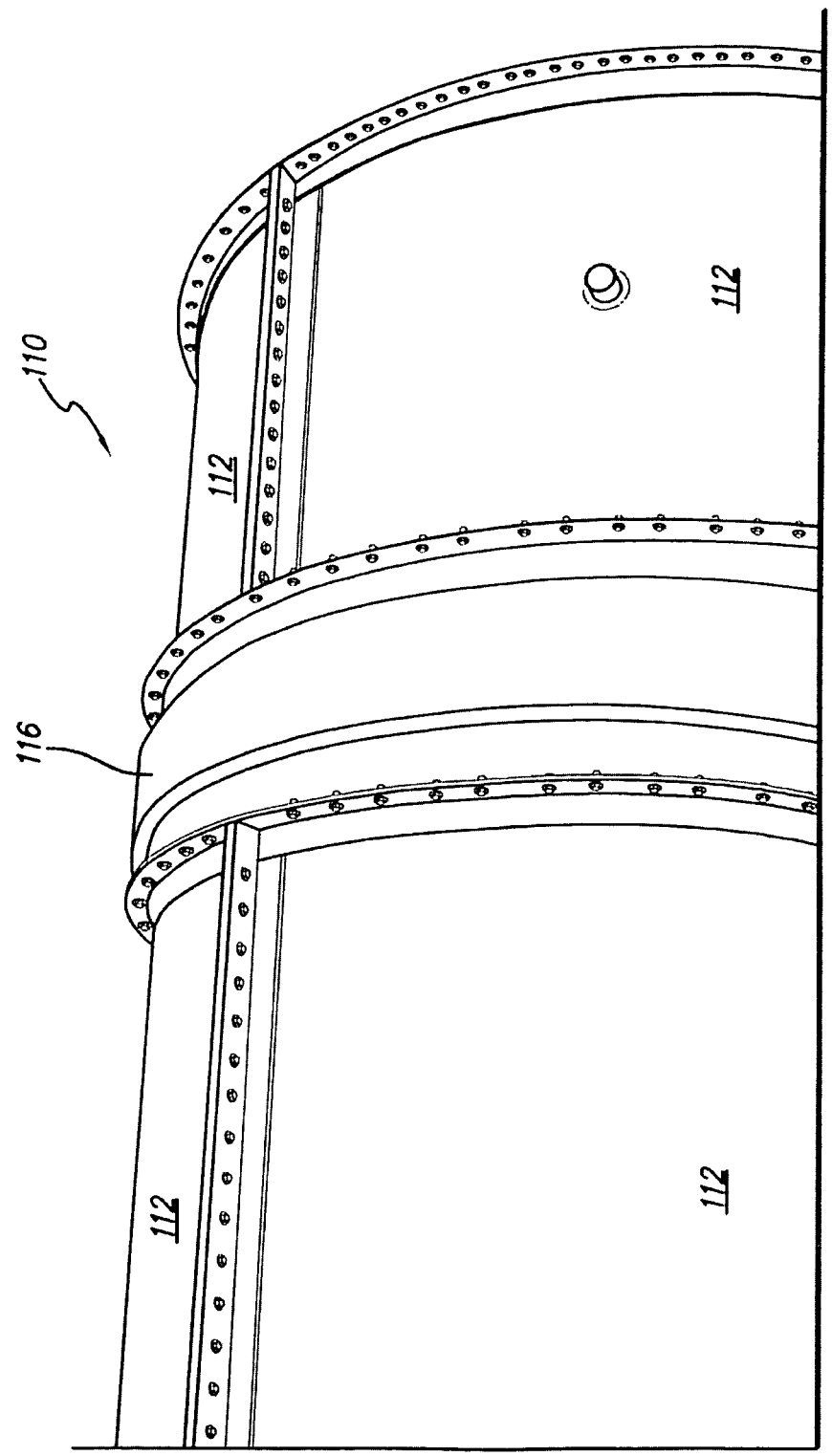
FIG. 10 is a perspective top view of the top of an exemplary drive tire of the present invention.
Figure 11:
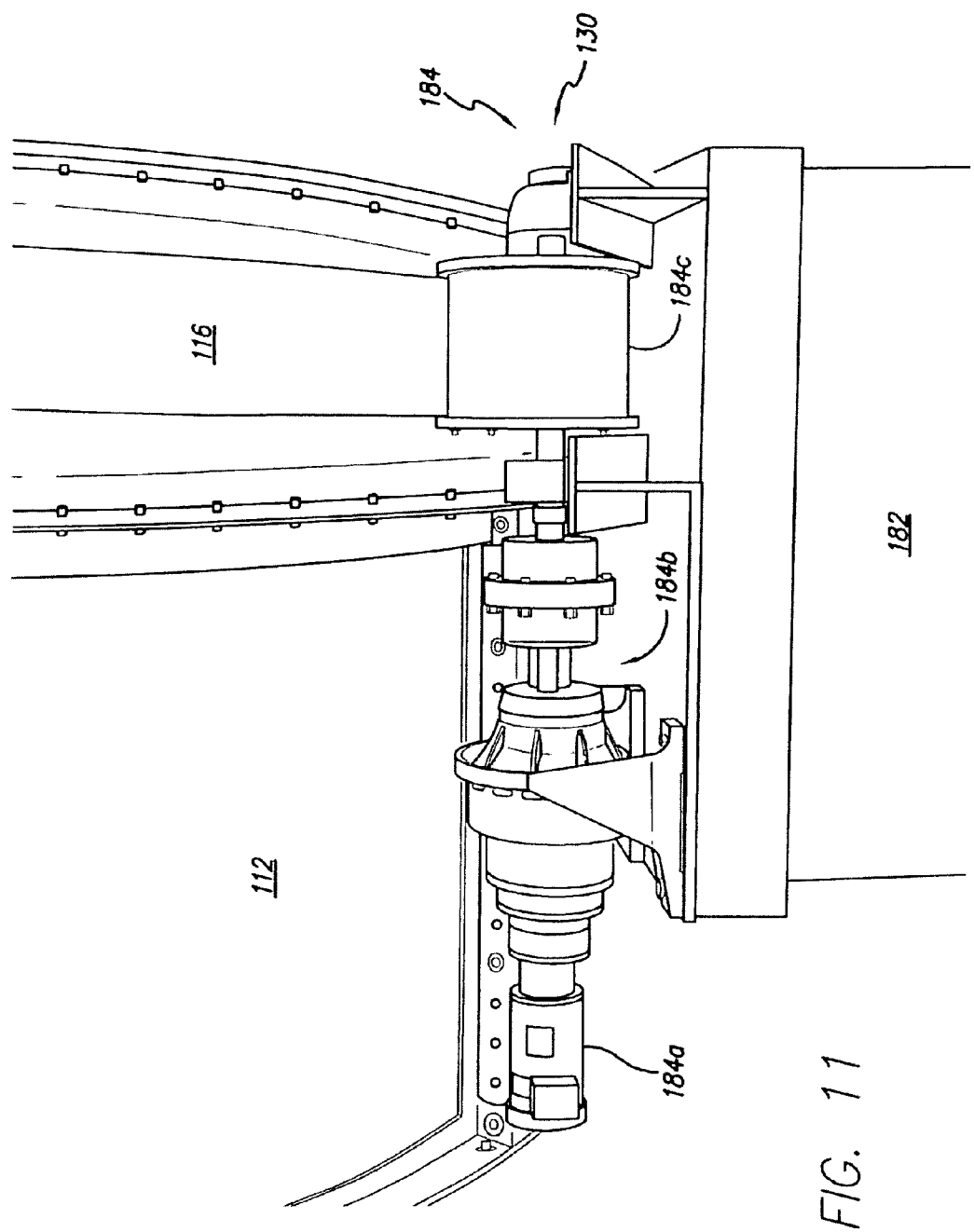
FIG. 11 is a perspective side view of an exemplary drive tire and an exemplary tangential rotational drive system in association with the drive tire.

Drive tires 116 (e.g. as shown in FIG. 8, FIG. 10, and FIG. 11) are the specifically designed sub-sections of the body of the drum cylinder 110 that support the tangential rotational drive system 130 (FIG. 11) for rotating the drum 110. In one preferred embodiment, the drive tires 116 are made from very heavy steel bands that function as the total load bearing member of the drum 110. The drive tires 116 may be made, for example, by rolling heavy steel and welding it to a lighter plate. Cross-members 132 (FIG. 8) may then be added for structural support and to ensure roundness. Preferably the cross-members 132 have a sufficiently small diameter or cross-section so that they do not affect the flow of materials through the drum 110. It should be noted that drive tires that are constructed from materials of sufficient strength may not need the cross-members 132. Rolled angle iron 122c (with holes added as set forth above) may be added to the drive tire 116 so that it can be used for bolting the drive tire 116 to adjacent panels 112. In one preferred embodiment, the drive tire 116 may be split apart into a plurality of arcuate sections 134a, 134b (shown as two). It should be noted that alternative embodiments of the drive tires may be a single unit or may be constructed of more than two arcuate sections. It should be noted that the rolled angle iron 122c and/or cross-members 132 may be added before or after the drive tire 116 is split into arcuate sections 134a, 134b. Fastening systems 136 (shown as two inwardly directed angle irons) may be used with the arcuate sections 134a, 134b of the drive tires 116 so that they can be connected (e.g. by bolting and/or welding at the seams) in the field. Preferably, the drive tires 116 are fabricated so that the pieces (e.g. the arcuate sections 134a, 134b and fastening systems 136) are interchangeable and can fit into a shipping container. Once in the field, the drive tires 116 may be connected (e.g. by bolting) to sub-cylinders 118 on either or both sides so that the resulting drive tire is able to handle load bearing capabilities.

The panels 112 and drum heads 114 can be painted and insulated as soon as they are complete. The drive tire 116 may or may not be painted and/or insulated. There is no need to assemble the entire drum (or to wait until all the components are complete) to paint and insulate. Traditionally the insulation used on in-vessel drum composters has been a multi-step polyurethane traditional foam insulation process. This multi-step insulation process begins after the drum has been constructed. Then the complete drum is sand-blasted and primed. The primed drum surfaces are covered with foam insulation which, in turn, is covered with a roof coating. The roof coating or "mud" is hand applied and is very labor intensive. Then the roof coating is painted. Although multi-step insulation will work with the present invention, preferred embodiments of the invention use an insulation that is a ceramic-impregnated paint-like insulating coating such as Delta T Industrial Coatings™ by Mascoat Products. One advantage of ceramic-impregnated paint insulation over other types of insulation is that it can be applied with traditional painting equipment. Ceramic-impregnated paint insulation may be applied in three or four coats. Another advantage of ceramic-impregnated paint insulation over other types of insulation is that it is only 0.06 inches (0.1524 centimeters) to 0.07 inches (0.1778 centimeters) as compared to 2 inches (5.08 centimeters) of traditional foam insulation. Yet another advantage of ceramic-impregnated paint insulation over other types of insulation is that it can be "touched up" with a brush in the field, which is not the case with traditional foam insulation.

Figure 6:
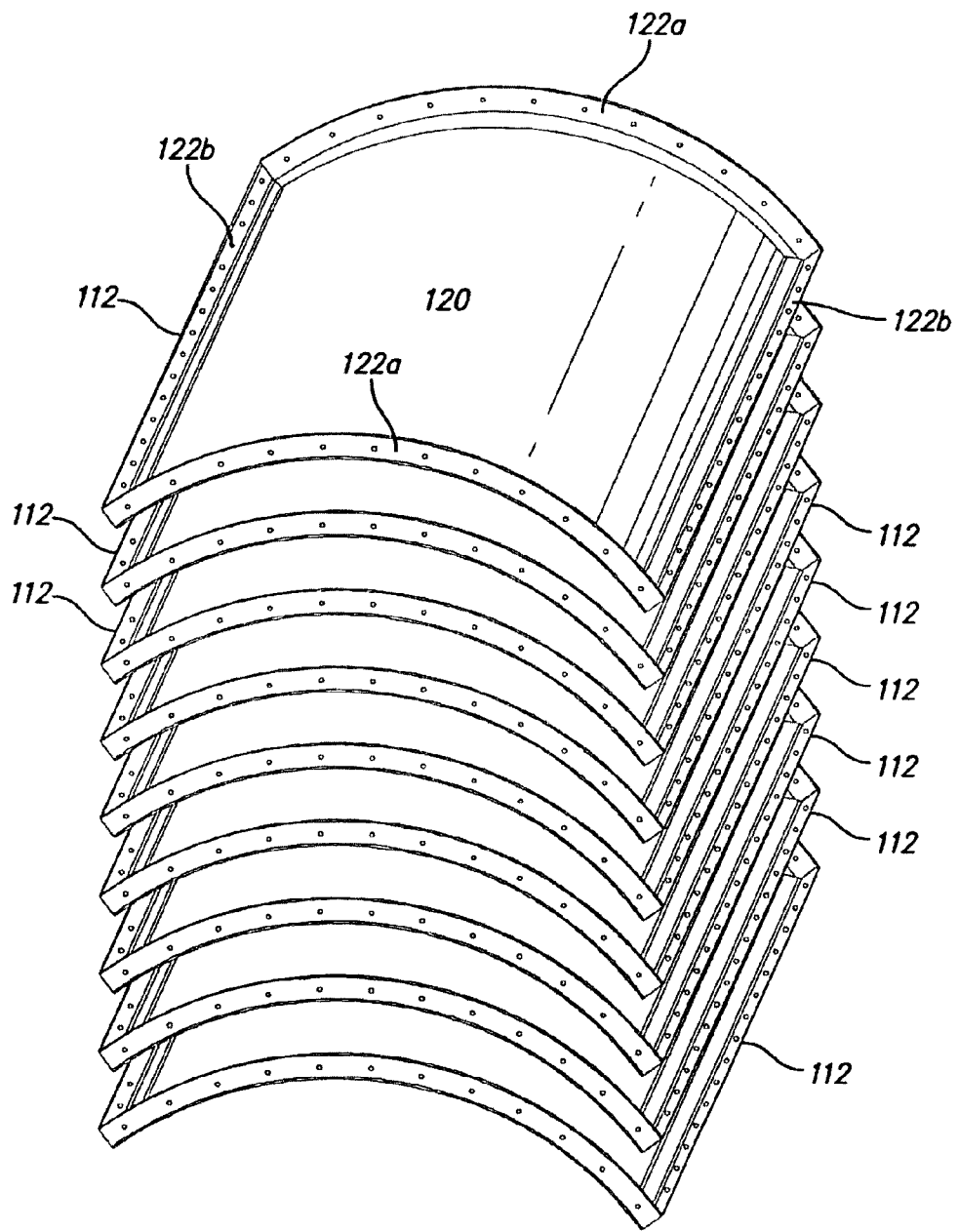
FIG. 6 is a perspective view of a stack of panels such as those shown in FIG. 4.

The panels 112 may be stacked together with other panels 112 (as shown in FIG. 6) so that the stacked panels 112 can easily fit into any shipping container and shipped anywhere in the world at standard shipping rates. The drive tires 116 and drum heads 114 also preferably can fit into a shipping container (or into the same shipping container as the panels 112). All components of a drum 110 are shipped to the end user. All components of a drum 110 are shipped to the installation site.

Fixtures and Panel Fabrication

Central to the panelized system of the present invention is the use of fixtures such as the novel cutting table 100 (FIG. 1), the novel multi-head drill press 102 (FIG. 2), the novel welding table 104 (FIG. 3), and other fixtures for fabrication of the panels 112 using the principles of mass production. The use of fixtures ensures substantial uniformity in the size and shape of the panels 112. Accordingly, in preferred embodiments of the invention, fixtures are used as much as possible in the fabrication process. A fixture is designed so that a task can be completed as quickly and as accurately as possible. Regardless of which panel design and/or drum design is chosen (see the "variations" section below), one of the significant advantages of the preferred embodiments of the present invention is that the panels 112 are interchangeable with each other and between drums. This is the basic premise of the mass production system. It should be noted that as the shape of the panel 112 is varied, the shape of the fixture is varied as well.

Prior to the invention of the cutting table 100 of the present invention, to cut a 20 foot (6.096-meter) section of rolled angle iron 122d into sections that are 100 inches (254 centimeters) long would be done using a cutting torch. The resulting 100-inch (254-centimeter) long section would then be placed in a welding fixture (that did not exist before the present invention) to mark the desired angles. The ends of the section would then be angled, again using a cutting torch. Finally slag would have to be ground off of the cut at the angled ends. It should be noted that, because angle iron 122d is already rolled into an arc, traditional chop saws or shears cannot ensure that the cuts are at the proper angle and ends would have to be hand-cut using a cutting torch.

Figure 1:
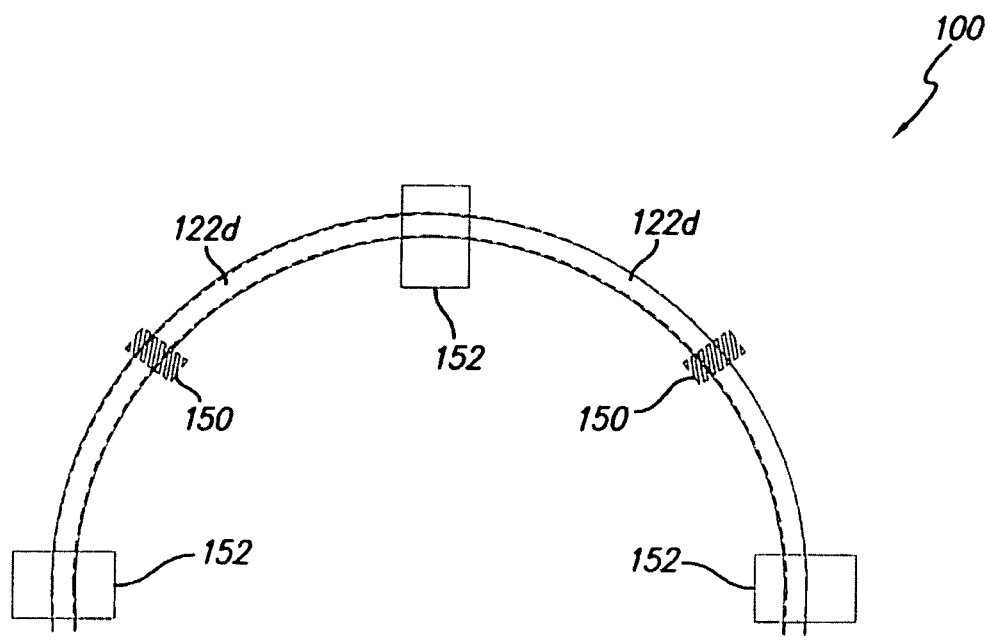
FIG. 1 is an overhead view of a cutting table with cutting devices.

The cutting table 100 of FIG. 1 is used to cut rolled angle iron 122d (e.g. a 20 foot (6.096 meters) section) so that it can be used as panel rolled angle iron 122a or drive tire rolled angle iron 122c. A cutting table 100 of the present invention preferably includes three primary components: support structure (not shown), securing apparatus 150 (e.g. clamps), and at least two cutting devices 152. The cutting table support surface may be a continuous planar surface (e.g. a table), one or more sets of "legs," or any other structure suitable to support the weight of the rolled angle iron 122d prior to cutting, during cutting, and after cutting. The securing apparatus 150 secures the rolled angle iron 122d directly or indirectly to the cutting table support structure. The at least two cutting devices 152 (shown as three cutting devices 152) may be, for example, the top part of a traditional chop saw (with the bottoms removed). The cutting devices 152 are spaced and angled so that when the rolled angle iron 122d is secured to the support structure and the cutting devices 152 are actuated, the rolled angle iron 122d will be cut at the exact length and angle required for its intended purpose. It should be noted that the cutting devices 152 may be automated to be simultaneously actuable.

Prior to the invention of the multi-head drill press 102 of the present invention, after each piece of rolled angle iron 122d was cut, it would be taken to a punch press and a first hole was punched. Then the first hole would be indexed onto a "stop" and the second hole would be punched. The second hole would then be indexed onto the stop and a third hole would be punched. This process would be repeated, typically eighteen times per piece. Once the holes were cut/punched, then the punched piece of rolled angle iron 122d would be taken to the welding fixture (that did not exist before the present invention) to ensure the angles and ends were correct. Further, the straight angle iron 122b similarly required holes. Because the straight angle iron 122b was not rolled, existing methods of cutting could be used. Also, there may be some equipment that already exists that could punch holes in straight angle iron 122b, but such equipment is generally expensive. The applicant of the present invention was unable to find anyone who would punch holes in the rolled angle iron 122d. Those he approached expressed the opinion that they would not be able to meet the level of precision required for this project. Similarly, the straight pieces appear to have similar problems as far as precision is concerned. The existing process for punching the holes in the flat baffle bars 119, flat plate 120, and the flat wedges 124a has problems similar to the problems associated with the rolled angle iron 122d. To realize just how significant this problem of precision hole punching is, one would have to realize that for an exemplary drum 110, approximately 3,984 holes, not including those associated with the drum heads 114 and the drive tires 116, would have to be drilled. The 3,984 holes would include 1,728 holes associated with the rolled angle iron 122d and 2,160 holes associated with the straight pieces (the straight angle iron 122b and the baffle bars 119). The figure of "1,728 holes" associated with the rolled angle iron 122d is calculated using an exemplary drum 110 with 96 pieces of rolled angle iron 122d, each piece having 18 holes drilled therein. The figure of "2,160 holes" associated with the straight pieces is calculated using an exemplary drum 110 with 3 sets of 18 holes per panel and 40 panels per composter. The following chart exemplifies the number of holes in an exemplary drum 110:

Clearly, a faster method of cutting this many holes is desirable.

| Section | Hole/ Section | Section/Panel | Panels/Ring | Ring/Unit | Total Holes |
|---|---|---|---|---|---|
| rolled angle | 18 | 2 | 4 | 10 | 1440 |
| straight angle | 16 | 2 | 4 | 10 | 1280 |
| Tires | 18 | 4 | 2 | 2 | 288 |
| End Plates | 18 | 1 | 4 | 2 | 144 |
| Angle end plate | 12 | 2 | 4 | 2 | 192 |
| Baffle Bars | 16 | 1 | 4 | 10 | 640 |
| Total Holes | | | | | 3984 |

The multi-head drill press 102 of the present invention includes support structure 160, securing apparatus 162 (e.g. clamps for securing angle iron pieces 122 to the support structure 160), and a plurality of simultaneously actuable drill heads 164. In one preferred embodiment, the drill heads 164 are standard drill heads 164 that are attached to spindles and/or gearing 166 so that one or two motors 168 can drive all the drill heads 164. (It should be noted that the term "drill heads" is meant to include any perforation mechanism including drills, punches, or any other means for creating a hole.) The multi-head drill press 102 of the present invention could be implemented for use either on straight pieces (e.g. the straight angle iron 122b, the baffle bars 119) or rolled pieces (e.g. rolled angle iron 122d). From the side, both configurations would look approximately the same (and therefore the shown side view would be the same for both embodiments). From the top, however, the configurations of the drill heads 164 would be different. Specifically, for the multi-head drill press 102 for use on straight pieces, the drill heads 164 would be arranged linearly. For the multi-head drill press 102 for use on rolled pieces, the drill heads 164 would be arranged in an arc. In one preferred embodiment, the multi-head drill press 102 is a dedicated machine that could punch holes in only straight pieces or rolled pieces. In another preferred embodiment, the multi-head drill press 102 is adaptable or modifiable so that it could punch holes in both the straight pieces and the rolled pieces. This adaptability or modifiability might be accomplished by allowing the drills to be orientable (positionable) or by having interchangeable "head supports" (each head support designed to work with a particular straight or rolled piece). Both the straight and the rolled multi-head drill press 102 serve the same purpose. The purpose is to drill all the holes in a particular piece of angle iron 122 at the same time. In one preferred embodiment, all the holes for a particular piece would be drilled in thirty seconds (one person) rather than in twelve minutes (three people working together for four minutes) or more for traditional methods. The multi-head drill press 102 would also help to ensure that all holes are properly spaced and substantially uniform.

Prior to the invention of the welding table 104 of the present invention, there was no way to ensure that all the pieces of a drum 110 would meet the required specifications before they were welded. Also, there was no way to accommodate the changes to shape and draw that occur when metal is heated.

The welding table 104 of the present invention is able to solve these problems—it is able to ensure that all the pieces of a drum 110 would meet the required specifications before they were welded and to accommodate the changes to shape and draw that occur when metal is heated during the welding process. In preferred embodiments, the welding table 104 includes support structure 170, securing apparatus 172 (e.g. plate press cylinders that may be, for example, air cylinders and/or hydraulic cylinders for securing rolled plate 120 and angle iron pieces 122 to the support structure 170), and a plurality of guides 174 (e.g. holes or marks). The shown support structure 170 is two parallel arced bars and spanning bars therebetween. The support structure 170, however, could have alternative configurations including a solid structure or any other structure suitable for supporting the separate pieces of the panel 112 prior to welding, during welding, and after welding. The support structure 170 would also have to be suitable to withstand the heat associated with the welding process. The guides 174 are used to confirm that the holes in the angle iron 122 are accurate. In the shown embodiment, there are guides 174 only on the two parallel arced bars, but in preferred embodiments there would be guides on the straight ends (e.g. the spanning bars) of the welding table 104. As each piece of angle iron 122 is placed on the welding table 104, a check can be done to ensure that the holes all match. This can be accomplished manually (by eye) or can be automated (e.g. using sensors positioned behind the holes in the fixture to verify that the holes are not blocked). The securing apparatus 172 is preferably mounted so as to be "movable" (e.g. in the directions shown by the arrows or in alternative directions) in FIG. 3 for loading and unloading. This would allow the securing apparatus 172 to be moved out of the way until the pieces of the panel 112 have been properly positioned (loaded) on the welding table 104. Once the pieces are in position, the securing apparatus 172 are positioned and actuated to provide pressure on the pieces of the panel 112. The securing apparatus 172 ensures that there is proper contact between the rolled plate 120 and the angle iron 122. The pressure both helps prevent the relative movement of the pieces during the welding process and helps the panel retain its shape during the heating process. After verification and securement, the pieces are welded, allowed to cool, and then removed from the welding table 104 (unloaded).

Using the fixtures described above, an exemplary fabrication process for constructing panels 112 (the panels used to create the drums 110 shown in FIGS. 12-17 (the "Angle Iron—Plate Design")) would include the following exemplary steps. In this exemplary method, plate steel is rolled and cut (this may be done off-site) to form the skin of the drum 110. The angle iron 122 is cut using the cutting table 100 or standard cutting means (for straight angle iron 122b). The rolled plate 120, angle iron 122, and other components may then be pre-drilled or pre-punched using the multi-head drill press 102. Then, using the welding table 104, the angle iron 122 is welded along the edges of the rolled plate 120 so that the panels 112 can be fastened together through the substantially perpendicular flange (to the rolled plate 120) of the angle iron 122. The following paragraphs give more of the specifics of some of these steps.

Both rolled plate 120 and angle iron 122 are rolled (if necessary) and cut to the proper radius and length. In order to ensure that the angle iron 122 is rolled and cut to the proper radius and length, the cutting table 100 is used. The rolled angle iron 122 is placed on the cutting table 100 and held with the securing apparatus 150 (clamping mechanism). If the angle iron 122 is not rolled to the proper radius, it is apparent when the angle iron 122 is placed on the cutting table 100. The radius has to substantially match before the long angle irons 122 are cut. Preferably, if the radius does not match, then the angle iron 122 is rejected and it is either re-rolled or scrapped. This angle iron 122 is then cut to the proper length and angle with a cutting devices 152 built into the cutting table 100. There may also be a cutting table for the straight angle iron 122b to ensure that not only are the straight angle irons 122b the exact same length, but that the cuts of the straight angle irons 122b are at the proper angle. The straight cutting table may also be used to cut the baffle bars 119 that go inside the drum 110 since it is imperative that the baffle bars 119 be substantially the same length as the straight angle iron 122b.

The angle iron 122 is then moved from the cutting table 100 to the appropriate multi-head drill press 102. There may be two different multi-head drill presses: one specific fixture for drilling holes in the rolled angle iron 122 (multi-head drill press 102) and one specific fixture for drilling holes in the straight angle iron 122 and baffle bars 119. It is absolutely critical that the holes are drilled or punched in the proper location and spacing. Accordingly, the rolled angle iron 122 is held in place with securing apparatus 162. Then the multi-headed drill press 102 simultaneously drills a plurality of holes (shown as 18 holes). Preferably, similar machines make holes in the straight angle iron 122b and baffle bars 119.

The welding table 104 is used to ensure that all the panel components are held firmly and to ensure that there is no "creep" in the welding process. "Creep" is the tendency of steel to change its shape when heated and cooled. The flanges or angle irons 122 are placed on the welding table 104 first. Using the guides 174 the holes of the angle irons 122 are checked. Then the rolled plate 120 is placed on top of the angle irons 122. The securing apparatus 172 presses down on the rolled plate 120 to ensure it remains in the proper place throughout the welding process. At this point, the radius of the rolled plate 120 may be checked to ensure it meets specifications. Once all the pieces are in place, aligned, and secured, the panel 112 may be welded around the perimeter of the rolled plate 120. Preferably the corners of the angle irons 122 are also welded. Additions to the panel 112 (e.g. doors, thermometer ports, or sample ports) may be added at this time. When the panel 112 is complete it is removed from the fixture and sent for paint and insulation (e.g. at a separate location, room, or station).

The drawbacks to the "Angle Iron-Plate Design" are that it is difficult to roll the angle iron 122 and to keep the angle iron 122 from "twisting." Angle iron 122 is also expensive (as compared to flat bar). The problems with rolling and twisting, however, can be overcome by forcing the rolled angle iron 122 "true" before cutting, drilling, punching, and/or welding. The drawbacks of using angle iron 120 are offset by the advantages. For example, one added benefit of using angle iron 120 is that it adds to the structural integrity of the drum 110. There are similar structural integrity advantages that would be available in using the "Flat Bar-Plate Design" (in which the angle iron 122 is replaced with flat bars), except that while the angle iron 122 is more expensive than the flat bar, the angle iron 122 has the advantage of being able to provide a wide tolerance of rolled plate 120 widths and concentricity (squareness). The rolled plates 120 come from the mill slightly oversized so that they can be squared before use. By using angle iron 122 as the edging rather than flat bar, the exact dimension or concentricity (squareness) of the plate no longer becomes an issue. Angle iron 122 allows for an overlapping joint. Since the dimension of the angle iron 122 in this exemplary embodiment is 4 inches (10.16 centimeters), the joint can be overlapped by 2 inches (5.08 centimeters). This allows for a 2-inch (5.08-centimeter tolerance around all the edges of the rolled plate 120. This means that it is irrelevant that the plate is, for example, 0.5 inches (1.27 centimeters) too wide or too narrow. On the other hand, when joining the flat bar to the rolled plate there must be a "butt weld." In order for a butt weld to work, the two pieces need to touch completely and there must be a gap of less than half the thickness of the plate—in this case, approximately 0.19 inches (approximately 0.4826 centimeters).

Drum Fabrication

FIGS. 12-17 show a drum 110 made according to the "Angle Iron—Plate Design."

Figure 12:
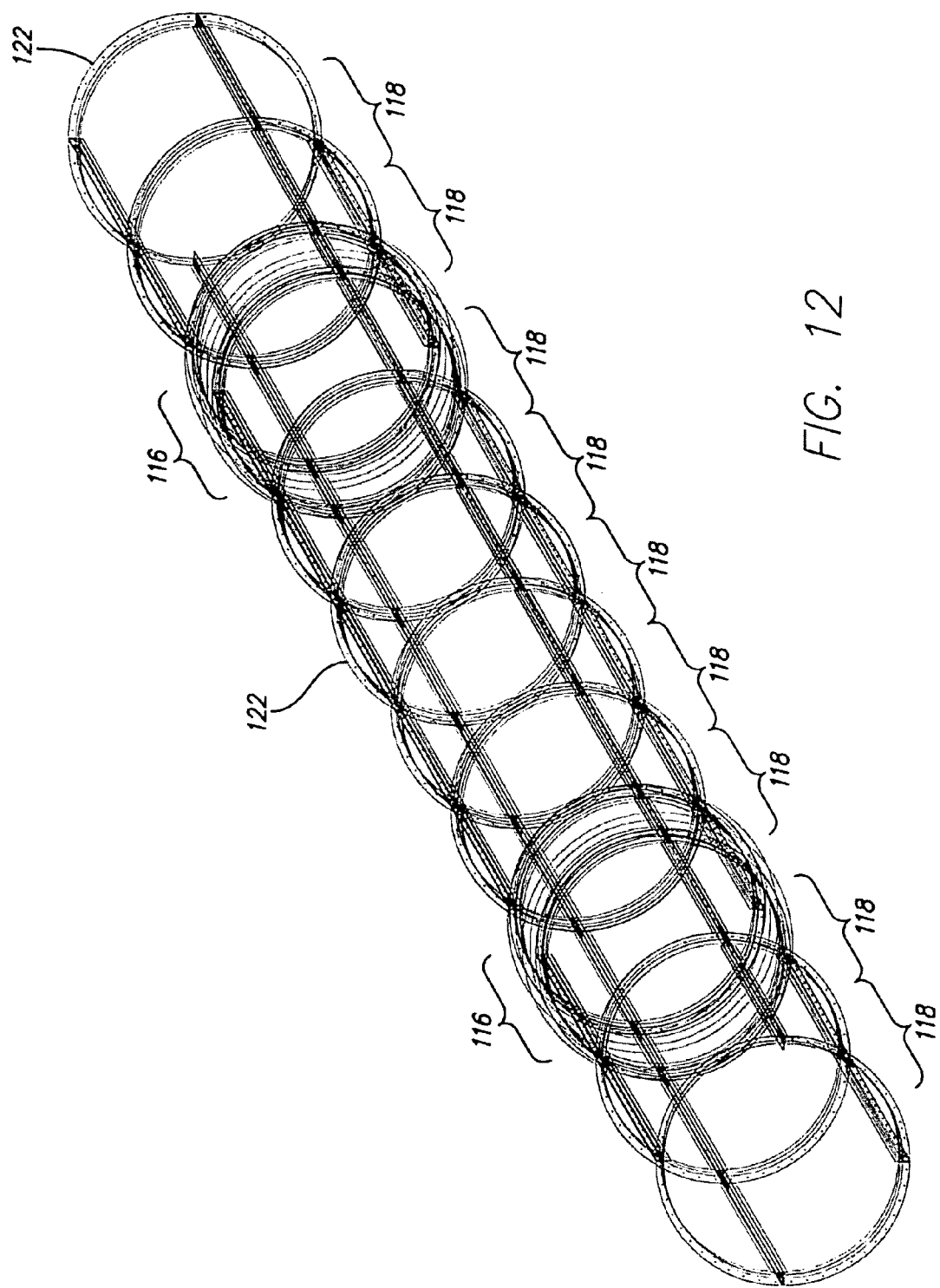
FIG. 12 is a perspective view of the angle iron and drive tires assembled into an exemplary drum cylinder.

FIG. 12 shows the angle iron 122 and drive tires 116 used to create an exemplary drum cylinder according to the "Angle Iron—Plate Design." This figure is for illustration purposes only as the "skeleton" would not be produced in preferred embodiments of the invention. In this embodiment, there are a total of 9 sub-cylinders 118 (36 panels 112) and 2 drive tires 116 that are arranged in the following order: 2 sub-cylinders 118, a drive tire 116, 5 sub-cylinders 118, a drive tire 116, and 2 sub-cylinders 118.

At the installation site, the components are removed from the container. The components are then bolted together "in the field." This assembly requires only a minimal amount of equipment (e.g. a forklift or sky track). It does not require expensive cranes and such because the drum 110 is assembled on one or more exemplary bases 182.

Figure 13:
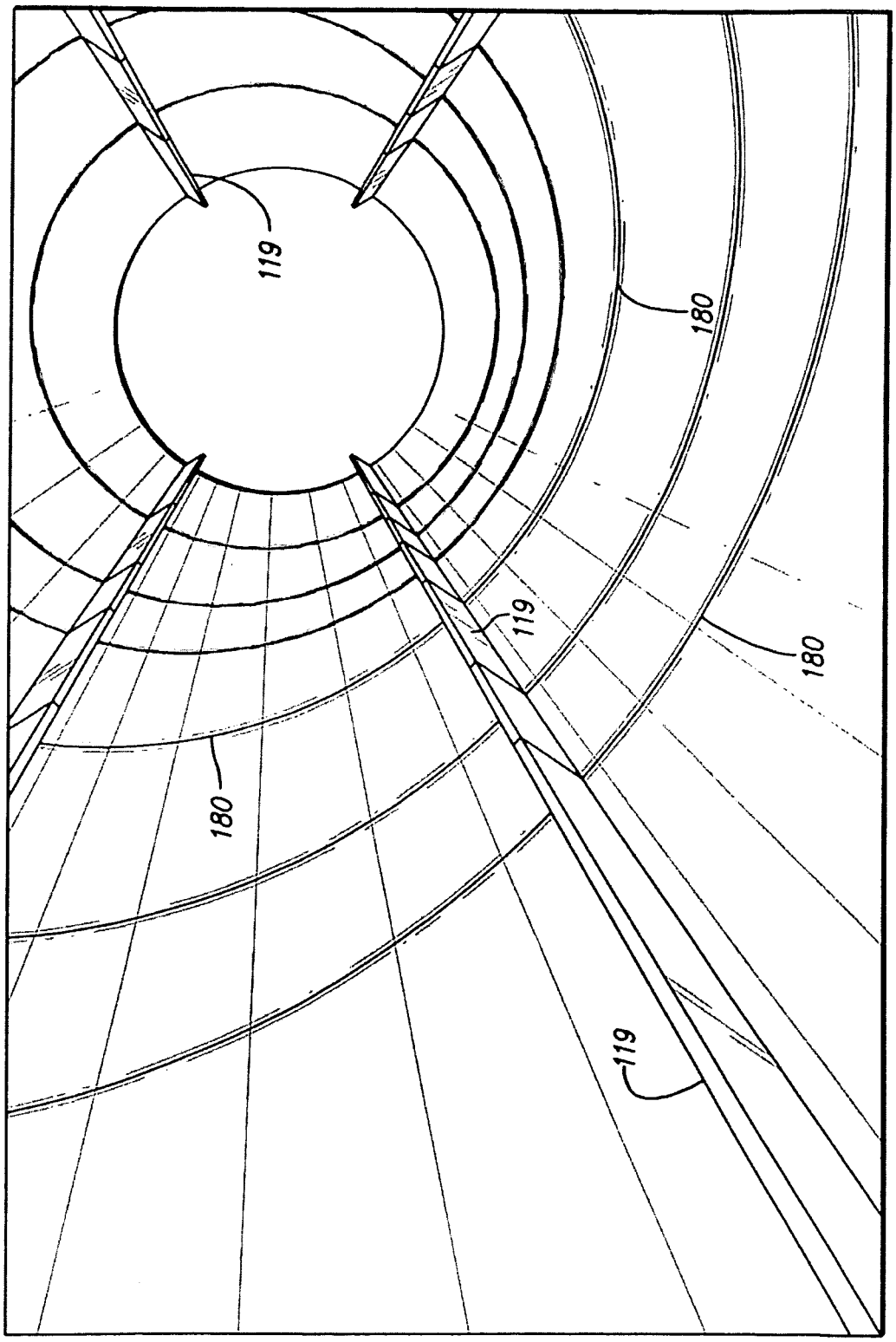
FIG. 13 is a perspective view of the interior of a drum cylinder (without a drum head) showing the sealing of the seams between the assembled sub-cylinders.
Figure 14:
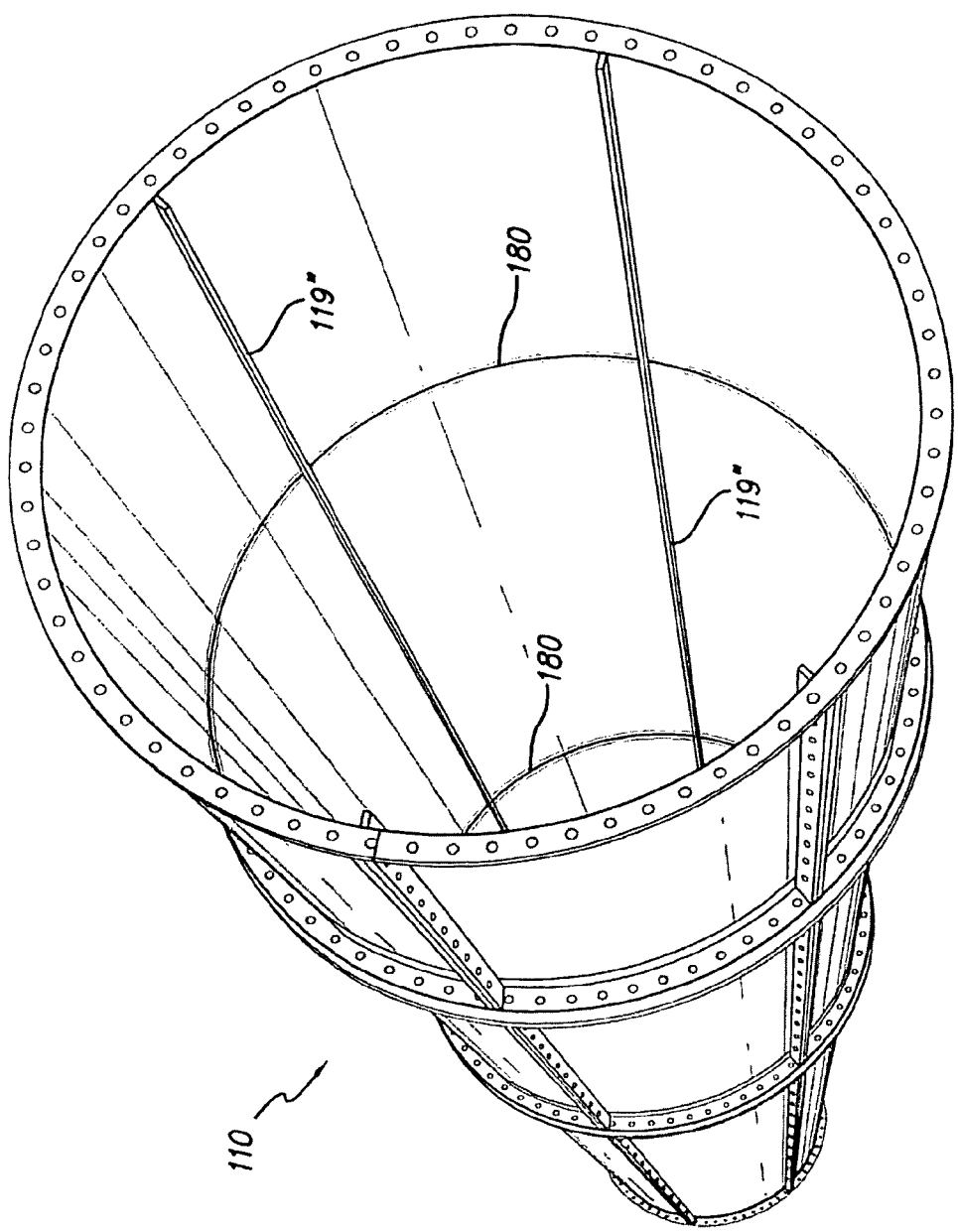
FIG. 14 is a perspective view of three assembled sub-cylinders with elongate baffle bars spanning the sub-cylinders.
Figure 15A:
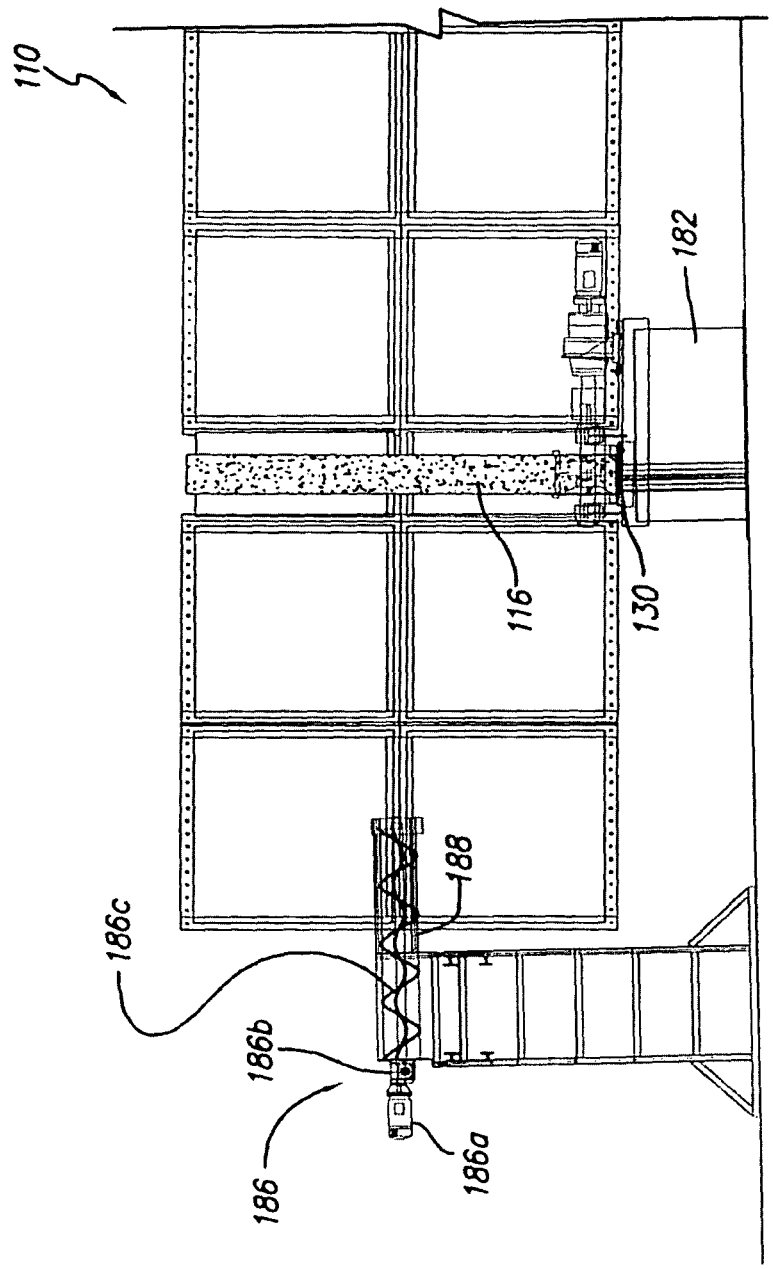
Figure 16:
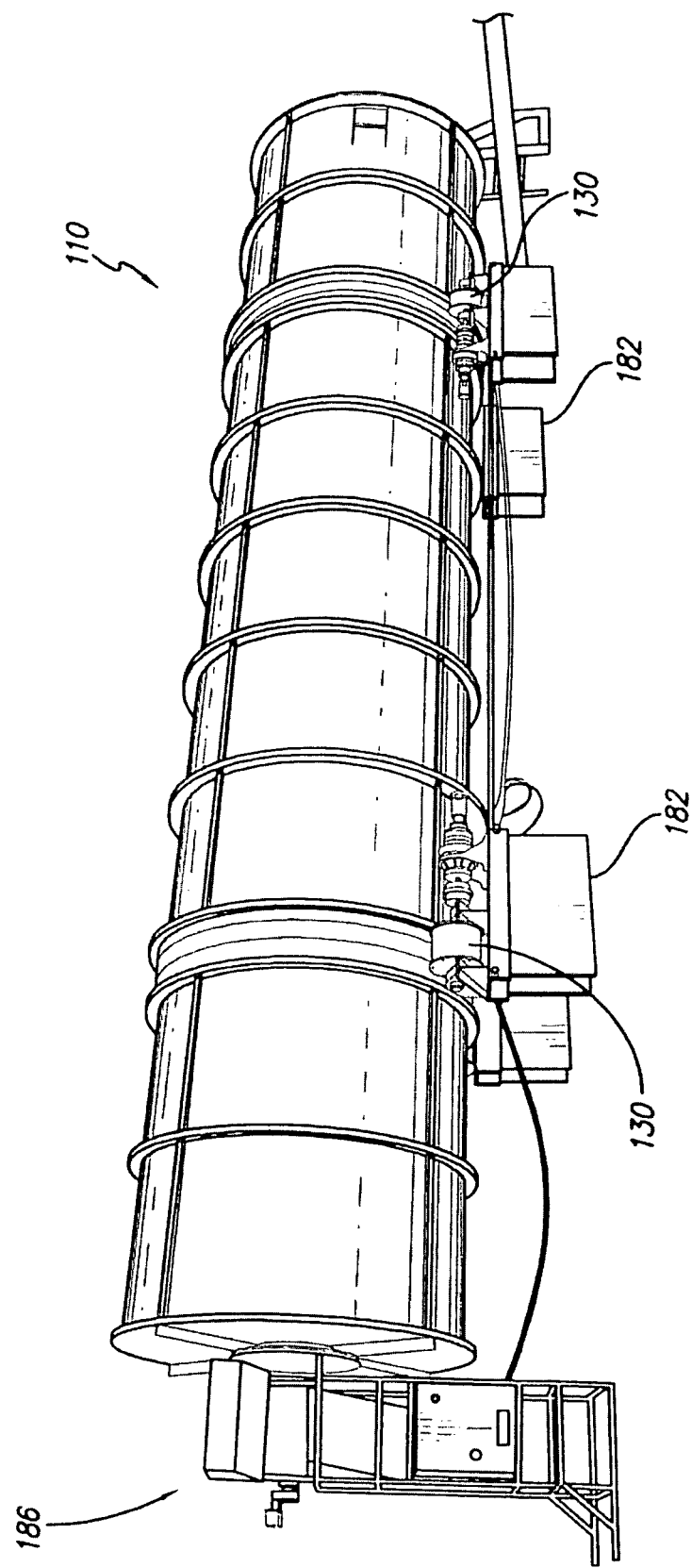
FIG. 16 is a perspective side view of an exemplary drum of the present invention.

In one preferred embodiment, the panels 112 are bolted together to form sub-cylinders 118. FIG. 5A shows three panels 112 assembled together to make three-quarters of a ring or sub-cylinder 118. As shown in FIG. 5B, adjacent panels of a sub-cylinder 118 are preferably separated by a baffle bar 119. Drive tires 116 (e.g. as shown in FIG. 8, FIG. 10, and FIG. 11) may be assembled in the field or may come pre-assembled. The sub-cylinders 118 and drive tires 116 are then bolted together to form the drum cylinder 110 having a first cylinder end with a first annular cylinder edge and a second cylinder end with a second annular cylinder edge. Drum heads 114 (such as those shown in FIG. 7A, FIG. 7B, and FIG. 9) may then be connected to the ends (the first and second annular cylinder edges) of the drum cylinder 110. Caulking 180 or other sealant may be added to the seams as shown in FIG. 13 and FIG. 14. Of course, a rotational drive system and material input mechanisms would also be needed to produce a functioning composter.

FIG. 13 and FIG. 14 show two variations on the fabrication of the drum 110. In FIG. 13 the baffle bars 119 are the same length as the width of the sub-cylinders 118. The baffle bars 119 can be aligned (as shown) or the baffle bars 119 can be staggered. Staggering would be accomplished by rotating each sub-cylinder 118 (prior to being attached to the adjacent sub-cylinder(s) 118) so that its baffle bars 119 were not adjacent to the baffle bars 119 of its adjacent sub-cylinder(s) 118. FIG. 14 shows the use of elongated baffle bars 119" that extend between multiple sub-cylinders 118. In such a configuration, the panels 112 would be added individually as opposed to drum fabrication where sub-cylinders are added.

Figure 17:
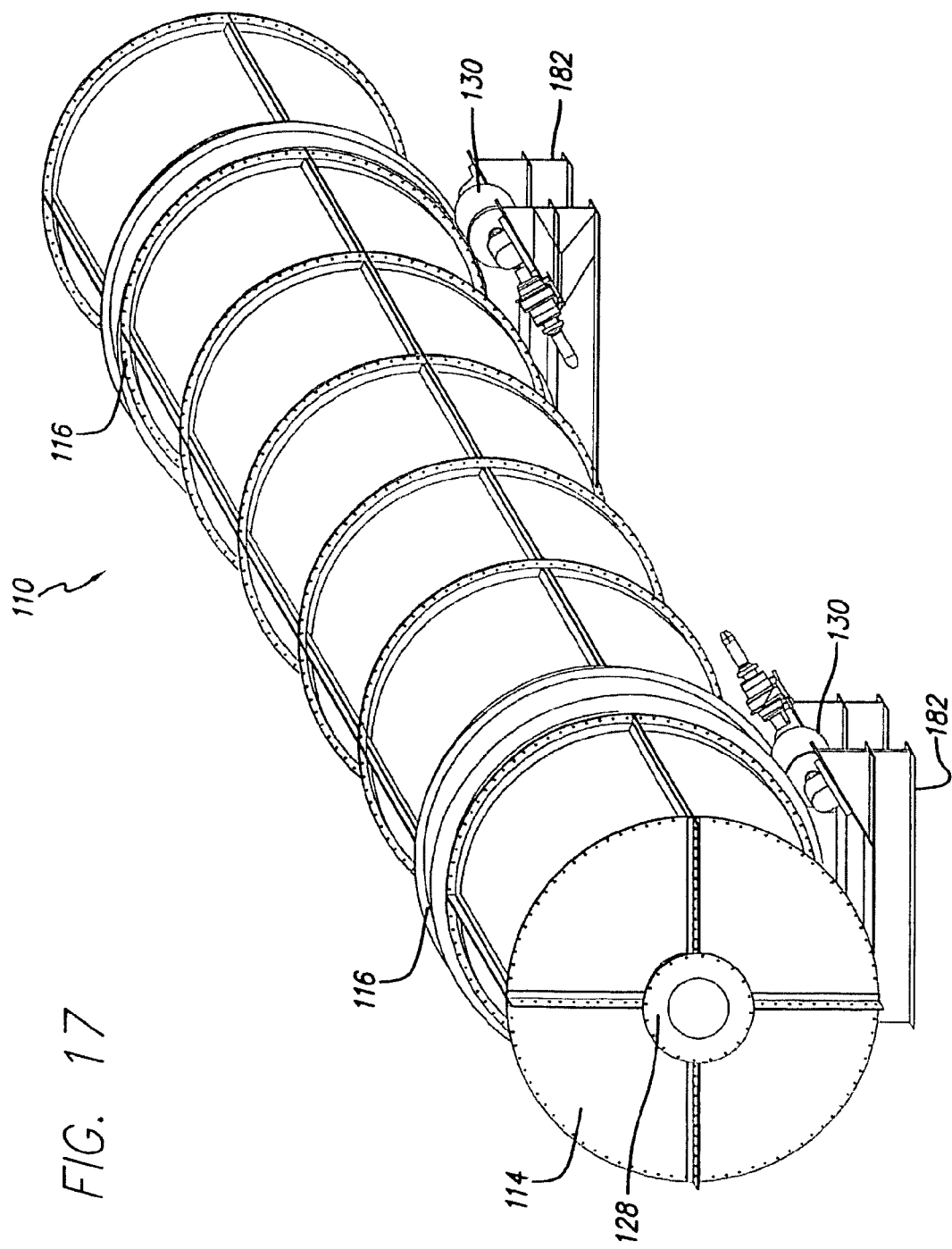
FIG. 17 is a perspective view of an alternative exemplary drum of the present invention with drum heads.

FIG. 12, FIG. 15A, FIG. 15B, and FIG. 16 all show an embodiment with a total of 9 sub-cylinders 118 (36 panels 112) and 2 drive tires 116 that are arranged in the following order: 2 sub-cylinders 118, a drive tire 116, 5 sub-cylinders 118, a drive tire 116, and 2 sub-cylinders 118. FIG. 17 shows an alternative embodiment with 7 sub-cylinders 118 (28 panels 112) and 2 drive tires 116 that are arranged in the following order: a sub-cylinder 118, a drive tire 116, 5 sub-cylinders 118, a drive tire 116, and a sub-cylinder 118. FIGS. 18A-19H show alternative embodiments with different numbers of sub-cylinders. Whereas FIGS. 18A-19H show embodiments having similar diameters (e.g. approximately 10 feet (approximately 3.048 meters)), FIG. 18I shows the drum having an alternative diameter (e.g. approximately 13 feet (approximately 3.962 meters)). The following chart shows the relationship between the number of sub-cylinders and the volume in cubic yards per day the respective composters could facilitate.

Figure 18A:
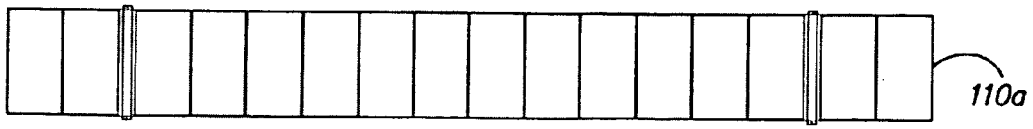
FIGS. 18A-18I are side views of exemplary simplified drums made according to the methods of the present invention, the drums being of various sizes.
Figure 18B:
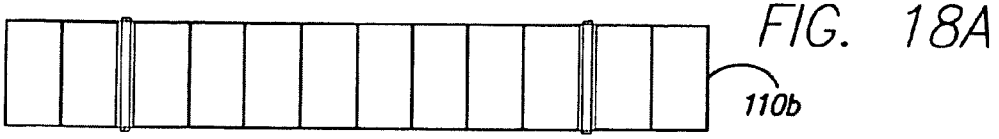
Figure 18C:
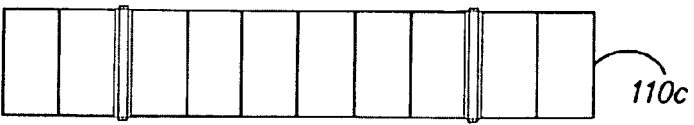
Figure 18D:
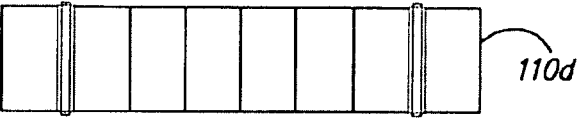
Figure 18E:
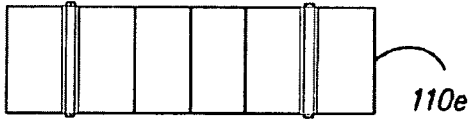
Figure 18F:
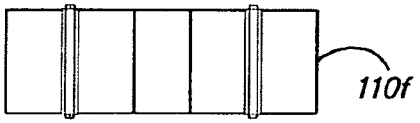
Figure 18G:
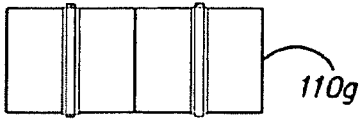
Figure 18H:
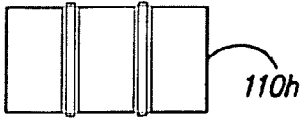
Figure 18I:
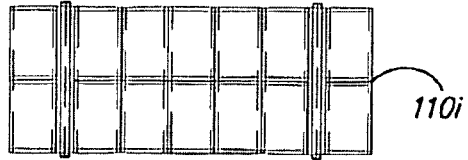

| Figure | Rings | Volume |
| --- | --- | --- |
| FIG. 18A | 16 | 54 |
| FIG. 18B | 12 | 41 |
| FIG. 18C | 10 | 34 |
| FIG. 18D | 8 | 28 |
| FIG. 18E | 6 | 21 |
| FIG. 18F | 5 | 18 |
| FIG. 18G | 4 | 15 |
| FIG. 18H | 3 | 12 |
| FIG. 18I | 7 | 34 |

The dimensions, numbers of sub-cylinders, number of drive tires, and diameters are meant to be exemplary and are not meant to limit the scope of the invention.

The rotation of drums for composters is typically accomplished using a direct rotational drive system (e.g. a "plurality of separate wheels/gear box combinations") to rotate the drum 110 of the composter. Most rotating drum composter manufacturers use a single large motor (e.g. 400 horsepower) that runs at slower speeds.

Preferred embodiments of the present invention, however, preferably use a tangential rotational drive system 130 in that it directly drives load-bearing wheels that are adjacent to the drive tires 112. As shown in FIG. 11, the tangential rotational drive system 130 of the present invention is preferably divided so that pairs of motor-gearbox-contacts 184 are positioned on either side of the bottom of the drive tires 116. The motor-gearbox-contacts 184 both support and rotate the drum 110. The motor-gearbox-contacts 184 include a motor 184a, a gearbox 184b, and a contact wheel or bearing 184c. The motor 184a provides power to the gearbox 184b that, in turn, rotates the contact wheel or bearing 184c. When the pairs of contact wheels or bearings 184c rotate in a coordinated fashion, the drive tires 116 thereon rotate. This causes the entire drum 110 to rotate. The tangential rotational drive system 130 of the present invention is shown as including four smaller motors 184a (e.g. 10 horsepower each) that run at their regular speed to get the required torque to rotate the drum 110. (Large reduction planetary gearboxes 184b are also preferably used. The overall reduction in speed from the motor 184a to the outside of the drum 110 can be as much as 36,000:1.) This reduces the electricity requirements needed to run the rotation of the drum 110. For example, the wattage difference between 400 horsepower (over 430 amps (103 kW)) and 40 horsepower (each 10 horsepower motor uses 14 amps (3.4 kW)) is a savings of 344 amps. The motors 184a are preferably electrically synchronized (e.g. tied together) so that they turn at the same speed. In addition to the energy savings, the tangential rotational drive system 130 of the present invention requires less maintenance than known direct rotational drive systems.

A composter incorporating the present invention may also include loading apparatus 186 (e.g. a motor 186a, a gearbox 186b, and a screw conveyor 186c), an air inlet 188 or fan, and an exhaust fan 190a and snorkel 190b. This structure or alternative structure would most likely be necessary to a functioning composter. The material flowing through a composter would be input into the input end of the drum 110 using, for example, loading apparatus 186. The input end is substantially closed, except for the opening 126 for the loading apparatus 186. An air inlet 188 or fan may also be positioned so that it can provide air through the opening 126. An exhaust fan 190a and snorkel 190b are preferably positioned at the output end of the drum 110.

Exemplary Advantages

The present invention is used to fabricate a rotating panelized drum 110 using the principles of mass production and allows for shipment on normal common carriers. Once it is in the field the rotating panelized drum 110 made according to the principles of the present invention operates like most of the composters that have already been patented. The panelized system, however, has many advantages including, but not limited to the following:

The majority, and possibly all, of the components of a panelized system of the present invention can be mass produced to lower the cost to fabricate the overall unit.

If the individual panel 112 becomes damaged, it is possible to replace individual panels 112 of a panelized drum 110 without having to resort to major construction. Panels 112 that become damaged through accident or normal abrasion can simply be unbolted, removed, and replaced.

The novel fixtures 100, 102, 104 ensure that the panels 112 are almost exactly the same in dimension and fit.

The panelized system of the present invention shortens lead times because components (panels 112, drum heads 114, drive tires 116, etc.) are fabricated separately. The components can all be started at the same time so instead of having to wait until the cylinder is complete to start on the drive tires 116 (a week long process), the drive tires 116 can be started simultaneously with the start of the fabrication of the panels 112. By the time a set of drive tires 116 is made, all the panels 112 will have been made and have gone through the several day insulating process so that the lead time can be shortened from eight weeks to one week.

Because components that are insulated are relatively small (e.g. a panel 112), the insulation process is less expensive than insulating an entire large drum 110.

The panelized system produces a rotating drum 110 that is more rigid (sturdy) than known rotating drums. A more rigid drum 110 keeps its roundness better.

The panel size can be varied to make composter drums 110 of various sizes, and the number of panels 112 can also be varied to give different size composters. A customer that orders a composter drum 110 of one size and then determines that he needs a larger size can be accommodated at any stage—including after the composter has been produced and installed.

All the components are small enough to alleviate the need for expensive cranes and material-handling equipment.

The panels 112 stack together for shipping and then form sub-cylinders 118 of a drum 110 when fastened together.

The panelized system of the present invention can be shipped using normal shipping containers or flat bed trailers not requiring special equipment or permits. All components are small enough so that they can be shipped via common carrier, thus reducing the overall shipping cost to the customer.

A rotating drum 110 using the panelized system can be fabricated in the field without having to be insulated in the field.

The panelized system results in more uniform drums 110.

Because of the previous fabrication processes and the way the steel is cut it is not uncommon to have a 50-foot (15.24-meter) drum 110 vary as much as 9 inches (22.86 centimeters) in length from one drum 110 to the next. This makes alignment difficult when they are not the same size. Roundness of the large drum 110 is also always an issue.

Variations

There are a number of variations in the panel and drum designs and also the panel and drum fabrication methods. It should be noted that the size and shape of the panels 112 and other components can also be adjusted many ways. In addition to the embodiments discussed above, four alternative embodiments are discussed below. It should be noted that the present invention also incorporates combinations of these embodiments.

The "Flat Bar-Plate Design." This embodiment is similar to the "Angle Iron-Plate Design" except that the angle iron 122 is replaced with flat bars. In this embodiment, flat bar steel (0.19 inches (approximately 0.4826 centimeters) thick×4 inches (10.16 centimeters) wide) in the unit length(s) shown in the figures is rolled the hard way (curved in the 4-inch (10.16-centimeter) direction and flat in the approximately 0.19-inch (approximately 0.4826-centimeter direction). The holes are punched and drilled to specifications. The rolled plate 120 is rolled as shown and described in relation to the "Angle Iron-Plate Design." The pieces are then secured to a welding table 104 and welded together.

Figure 19:
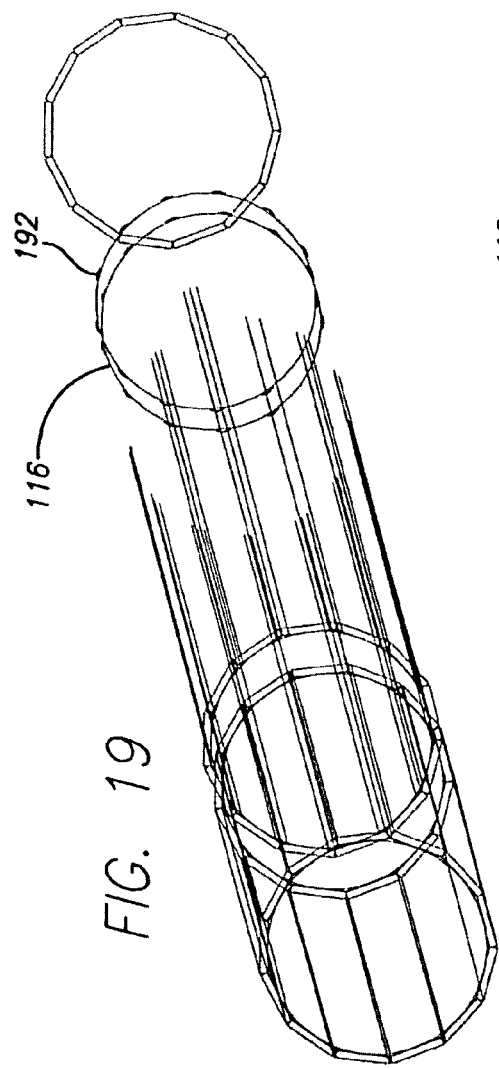
FIG. 19 is an expanded perspective view of an exemplary embodiment using a "Zeppelin Design."

The "Zeppelin Design." This embodiment, as shown in FIG. 14 and FIG. 19, uses a skeletal structure. In these embodiments, heavy steel-framed elongated baffle bars are precut and punched in a way that, when assembled at the job site, would form a skeletal structure for the drum 110 with a lighter "skin" of metal (e.g. panels) that attaches to the heavy structure. In the embodiment shown in FIG. 19, gaps between panels that are adjacent to the drive tire 116 can be sealed using small cut-outs 192.

Figure 20:
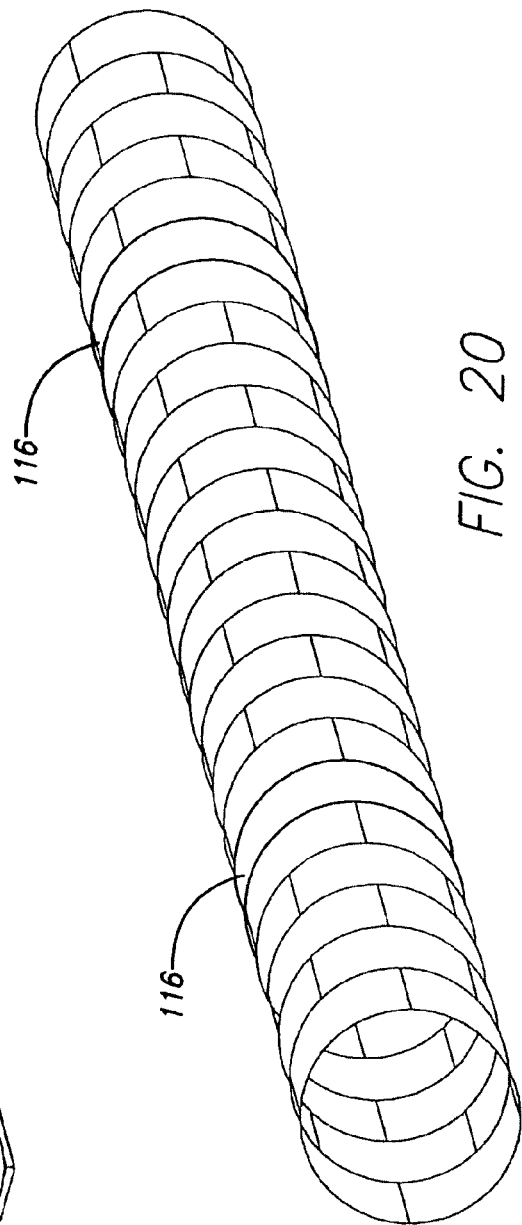
FIG. 20 is a perspective view of an exemplary embodiment using a "Horizontal Silo Design."

The "Horizontal Silo Design." This embodiment, as shown in FIG. 20, may use thinner metal than other embodiments. The sheets of steel may also be formed on forming machines similar to existing equipment that is used in the silo industry today. The panels are made of galvanized steel to reduce corrosion. In this embodiment the panels themselves may be smaller and/or narrower. Also, the panels may be staggered.

Figure 21B:
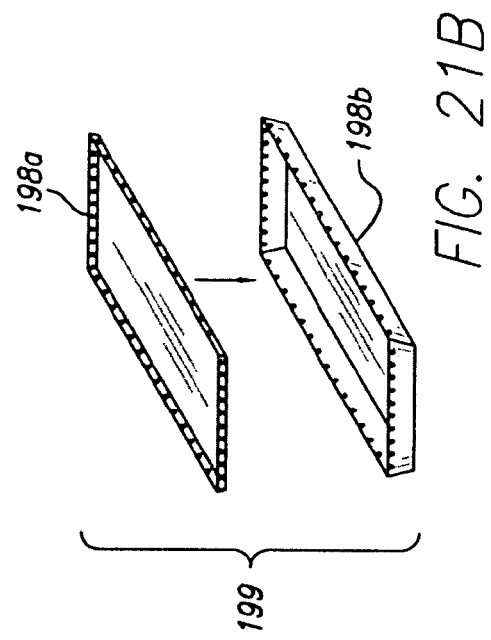
FIG. 21B is an expanded perspective view of a separated "cookie sheet" and "cake pan" of the "Cookie Sheet—Cake Pan Design."
Figure 21A:
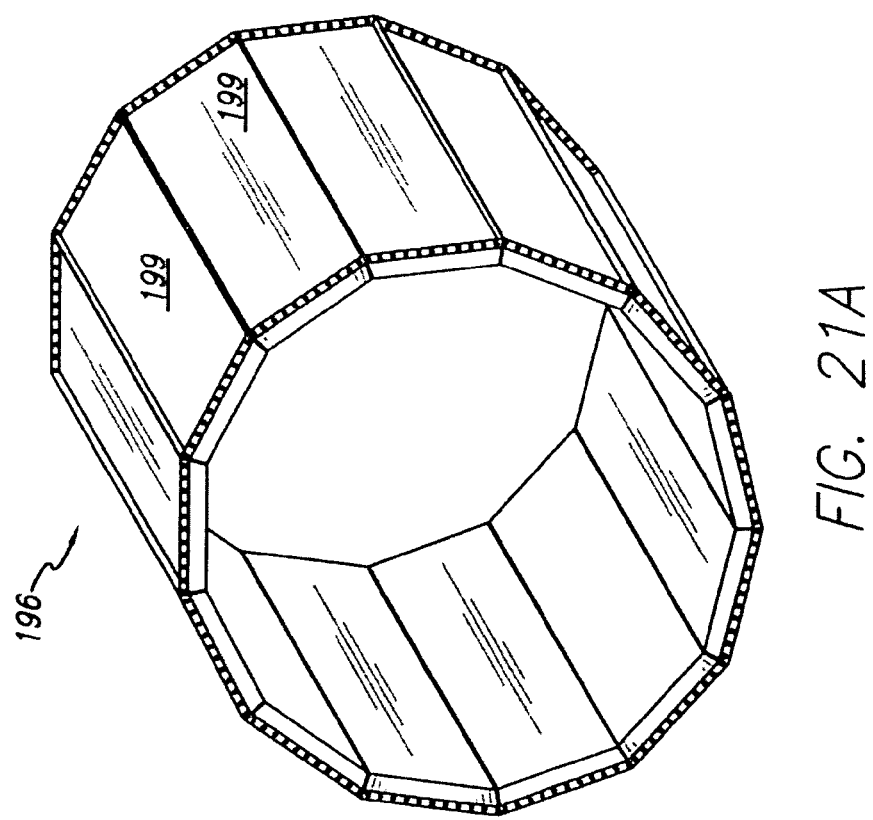
FIG. 21A is a perspective view of a sub-cylinder that may be used in an exemplary embodiment using a "Cookie Sheet—Cake Pan Design."

The "Cookie Sheet-Cake Pan Design." A sub-cylinder 196 of this embodiment is shown in FIG. 21A. FIG. 21B is an exploded view of a panel 199 that includes a "cookie sheet" 198*a* and "cake pan" 198*b*. In this embodiment, rolls of sheet steel are used on a "transfer press"-type assembly line. The steel is unrolled and moved along the press line and is formed in various steps like stamping out a car fender or hood. Two different plates are stamped: the cookie sheet 198*a* and the cake pan 198*b*. Holes are punched (or otherwise made) in the sides of both the pieces 198*a*, 198*b* to exact specifications. The result is a shallow piece (cookie sheet 198*a*) with holes and a deep wedge-shaped piece (cake pan 198*b*) with holes. The cake pan 198*b* is wedge shaped because the sides are angled outwards. The cookie sheet 198*a* fits inside the cake pan 198*b* and then a polyurethane foam insulation is injected between them. This insulation actually helps laminate the two pieces together so that they form a double wall panel 199. The double sides can be thought of as a frame and the laminated double bottom can be thought of as a skin that spans the opening created by the frame (a spanning skin). These panels 199 are wedge-shaped and, when bolted side-by-side, they form a sub-cylinder 196 (FIG. 21A). The cookie sheet 198*a* and cake pan 198*b* may be made of materials such as stainless steel or galvanized steel for longer life.

Miscellaneous

Connectors may vary. For example, it should be noted that the term "bolts" and "bolted" are used to describe connection mechanisms. It should be noted, however, that alternative connection mechanisms are included in the scope of the present invention. For example, alternative connection mechanisms may include cold welds, epoxy, rivets, clips, and other secure fasteners.

Although the panelized system is described in terms relating to the fabrication of composters, the technology has applications in other fields of drum 110 and tank fabrication. For the sake of this discussion, a drum 110 is a round rotating cylinder and a tank is a stationary cylinder. This is mainly dealing with horizontal tanks.

It should be noted that although the rotating drums 110 constructed in accordance with the present invention may be used as a composting rotating drum 110, they may also be used in other processes. For example, a rotating drum 110 constructed in accordance with the present invention may be used in other rotating drum 110 applications such as rice and sugar drying.

The descriptions and applications herein are not to be construed as limiting the invention, but as examples and illustrations of the invention. It should be noted that relative terms (e.g. first and second) are meant to help in the understanding of the technology and are not meant to limit the scope of the invention. Similarly, the term "front" is meant to be relative to the term "back" and the term "top" is meant to be relative to the term "bottom." It should be noted that the term "adjacent" is meant to mean "next to" and not necessarily to include "touching."

The terms and expressions that have been employed in the foregoing specification are used as terms of description and not of limitation, and are not intended to exclude equivalents of the features shown and described. This application is intended to cover any adaptations or variations of the present invention. It will be appreciated by those of ordinary skill in the art that any arrangement that is calculated to achieve the same purpose may be substituted for the specific embodiment shown. It is also to be understood that the following claims are intended to cover all of the generic and specific features of the invention herein described and all statements of the scope of the invention which, as a matter of language, might be said to fall therebetween.

What is claimed is:

1. A rotating drum having a large size precluding non-installation-site assembly to an assembled generally cylindrical form and transportation in said assembled generally cylindrical form to an installation site comprising:
    (a) a plurality of panels, each panel including a frame and a spanning skin, said frame having a first frame end, a second frame end, a first frame side, and a second frame side, each of said first and second frame ends having a plurality of holes, sized to receive non-hot-welded connectors, each of said panels having a shop-applied coating thereon prior to assembly of said panels;
    (b) a plurality of non-hot-welded connectors disposed in said holes in said first and second frames ends, to connect said first and second frame ends, at an installation site;
    (c) a sub-cylinder formed from at least two of said plurality of panels, for each panel at least one non-hot-welded connector connected at the non-shop installation site connecting said first frame end of said frame to said second frame end of an adjacent frame, the first frame ends of said at least two of said plurality of panels in said sub-cylinder forming a first sub-cylinder annular side, and the second frame ends of said at least two of said plurality of panels in said sub-cylinder forming a second sub-cylinder annular side;
    (d) a drum cylinder finder formed from at least two of said sub-cylinders, a plurality of said hot non-welded connectors being used to connect a first sub-cylinder annular side of a first sub-cylinder to a second sub-cylinder annular side of a second sub-cylinder, said drum cylinder having a first cylinder end with a first annular cylinder edge and a second cylinder end with a second annular cylinder edge;
(e) a first drum head, said first drum head connectable to said first annular cylinder edge;
(f) a second drum head, said second drum head connectable to said second annular cylinder edge; and
(g) a rotatable driver to rotate said rotating drum;
wherein said first and second frame ends include outwardly protruding legs; and wherein said plurality of non-hot-welded connectors disposed in said holes in said first and second frame ends extend through said outwardly protruding legs such that said non-hot welded connectors are fully outside of the interior of said drum.

2. The rotating drum defined in claim 1, further comprising a plurality of removable baffle bars including a portion extending into the interior of said drum, and a portion sandwiched between said outwardly protruding legs of said frame ends and held in place by means of said non-hot-welded connectors.

3. The rotating drum of claim 1, said spanning skin being rolled flat plate, said first frame end and said second frame end being straight angle iron, and said first frame side and said second frame side being rolled angle iron.

4. The rotating drum of claim 1 wherein said frame and said spanning skin are integral.

5. The rotating drum of claim 1, further comprising at least one drive tire, each said at least one drive tire positioned between two of said sub-cylinders.

6. The rotating drum of claim 1 wherein said sub-cylinder is formed from at least three of said plurality of panels.

7. The rotating drum of claim 1 wherein said sub-cylinder is formed from at least four of said plurality of panels.

8. The rotating drum of claim 1 further comprising a plurality of baffle bars, each baffle bar secured between said first frame end of said frame and said second frame end of an adjacent frame using said at least one connector.

9. The rotating drum of claim 1 wherein said rotational means is a tangential rotational drive system.

10. A rotating drum having a large size precluding non-installation-site assembly to an assembled generally cylindrical form and transportation in said assembled generally cylindrical form to an installation site comprising:
(a) a plurality of panels, each panel including a frame and a spanning skin, said frame having a first frame end, a second frame end, a first frame side, and a second frame side, each of said first and second frame ends having a plurality of holes, sized to receive non-hot-welded connectors, each of said panels having a shop-applied coating thereon prior to assembly of said panels;
(b) a plurality of non-hot-welded connectors disposed in said holes in said first and second frames ends, to connect said first and second frame ends, at an installation site;
(c) a sub-cylinder formed from at least two of said plurality of panels, for each panel at least one non-hot-welded connector connected at the non-shop installation site connecting said first frame end of said frame to said second frame end of an adjacent frame, the first frame ends of said at least two of said plurality of panels in said sub-cylinder forming a first sub-cylinder annular side, and the second frame ends of said at least two of said plurality of panels in said sub-cylinder forming a second sub-cylinder annular side;
(d) a drum cylinder formed from at least two of said sub-cylinders, a plurality of said hot non-welded connectors being used to connect a first sub-cylinder annular side of a first sub-cylinder to a second sub-cylinder annular side of a second sub-cylinder, said drum cylinder having a first cylinder end with a first annular cylinder edge and a second cylinder end with a second annular cylinder edge;
(e) a first drum head, said first drum head connectable to said first annular cylinder edge;
(f) a second drum head, said second drum head connectable to said second annular cylinder edge; and
(g) a rotatable driver to rotate said rotating drum;
wherein said spanning skin is rolled flat, and said first and second frame ends are comprised of angle iron having first legs that are permanently attached to the spanning skin and second legs protruding outwardly from the convex surface of the spanning skin, said plurality of non-hot-welded connectors being disposed in said holes in said first and second frame ends and extending through said outwardly protruding legs such that said non-hot welded connectors are fully outside of the interior of said drum.

11. The rotating drum defined in claim 10, wherein each of said sub-cylinders has a diameter of at least 10 feet when assembled and is assembled at the installation site by interconnection without welding of at least three substantially identical shop-fabricated and shop-coated panels.

12. The rotating drum defined in claim 10, further comprising a plurality of removable baffle bars including a portion extending into the interior of said drum, and a portion sandwiched between said outwardly protruding legs of said frame ends and held in place by means of said non-hot-welded connectors.

13. A rotating drum comprising:
(a) a plurality of panels, each panel including a frame and a spanning skin, said frame having a first frame end, a second frame end, a first frame side, and a second frame side, each of said first and second frame ends having a plurality of holes, sized to receive non-hot-welded connectors;
(b) a plurality of non-hot-welded connectors disposed in said holes in said first and second frames ends, to connect said first and second frame ends;
(c) a sub-cylinder formed from at least two of said plurality of panels, for each panel at least one non-hot-welded connector connecting said first frame end of said frame to said second frame end of an adjacent frame, the first frame ends of said at least two of said plurality of panels in said sub-cylinder forming a first sub-cylinder annular side, and the second frame ends of said at least two of said plurality of panels in said sub-cylinder forming a second sub-cylinder annular side;
(d) a drum cylinder formed from at least two of said sub-cylinders, a plurality of said hot non-welded connectors being used to connect a first sub-cylinder annular side of a first sub-cylinder to a second sub-cylinder annular side of a second sub-cylinder, said drum cylinder having a first cylinder end with a first annular cylinder edge and a second cylinder end with a second annular cylinder edge;
(e) a first drum head connectable to said first annular cylinder edge;
(f) a second drum head connectable to said second annular cylinder edge; and
(g) a rotatable driver to rotate said rotating drum;

wherein said first and second frame ends include outwardly protruding legs; and wherein said plurality of non-hot-welded connectors disposed in said holes in said first and second frame ends extend through said outwardly protruding legs such that said non-hot welded connectors are fully outside of the interior of said drum.

14. The rotating drum of claim 13, said spanning skin being rolled flat plate, said first frame end and said second frame end being straight angle iron, and said first frame side and said second frame side being rolled angle iron.

15. The rotating drum of claim 13 wherein said frame and said spanning skin are integral.

16. The rotating drum of claim 13, further comprising at least one drive tire, each said at least one drive tire positioned between two of said sub-cylinders.

17. The rotating drum of claim 13 wherein said sub-cylinder is formed from at least three of said plurality of panels.

18. The rotating drum of claim 13 further comprising a plurality of baffle bars, each baffle bar secured between said first frame end of said frame and said second frame end of an adjacent frame using said at least one connector.

19. The rotating drum of claim 13 wherein said rotational means is a tangential rotational drive system.

20. A rotating drum comprising:
  (a) a plurality of panels, each panel including a frame and a spanning skin, said frame having a first frame end, a second frame end, a first frame side, and a second frame side, each of said first and second frame ends having a plurality of holes, sized to receive non-hot-welded connectors;
  (b) a plurality of non-hot-welded connectors disposed in said holes in said first and second frames ends, to connect said first and second frame ends;
  (c) a sub-cylinder formed from at least two of said plurality of panels, for each panel at least one non-hot-welded connector connecting said first frame end of said frame to said second frame end of an adjacent frame, the first frame ends of said at least two of said plurality of panels in said sub-cylinder forming a first sub-cylinder annular side, and the second frame ends of said at least two of said plurality of panels in said sub-cylinder forming a second sub-cylinder annular side;
  (d) a drum cylinder formed from at least two of said sub-cylinders, a plurality of said hot non-welded connectors being used to connect a first sub-cylinder annular side of a first sub-cylinder to a second sub-cylinder annular side of a second sub-cylinder, said drum cylinder having a first cylinder end with a first annular cylinder edge and a second cylinder end with a second annular cylinder edge;
  (e) a first drum head connectable to said first annular cylinder edge;
  (f) a second drum head connectable to said second annular cylinder edge; and
  (g) a rotatable driver to rotate said rotating drum;
  wherein said spanning skin is rolled flat, and said first and second frame ends are comprised of angle iron having first legs that are permanently attached to the spanning skin and second legs protruding outwardly from the convex surface of the spanning skin, said plurality of non-hot-welded connectors being disposed in said holes in said first and second frame ends and extending through said outwardly protruding legs such that said non-hot welded connectors are fully outside of the interior of said drum.

21. The rotating drum of claim 20, further comprising at least one drive tire, each said at least one drive tire positioned between two of said sub-cylinders.

22. The rotating drum of claim 20 further comprising a plurality of baffle bars, each baffle bar secured between said first frame end of said frame and said second frame end of an adjacent frame using said at least one connector.

23. The rotating drum of claim 20 wherein said rotational means is a tangential rotational drive system.

* * * * *